United States Patent
Lum et al.

(10) Patent No.: US 9,789,265 B2
(45) Date of Patent: Oct. 17, 2017

(54) MEDICAL DEVICE ASSEMBLY

(71) Applicant: Becton, Dickinson and Company, Franklin Lakes, NJ (US)

(72) Inventors: Chee Leong Lum, Pequannock, NJ (US); Waheed Abid, Valley Stream, NY (US); Peter Douglas, Hillsdale, NJ (US); Ivan Zivkovic, Mahwah, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 233 days.

(21) Appl. No.: 14/537,999

(22) Filed: Nov. 11, 2014

(65) Prior Publication Data

US 2015/0065957 A1   Mar. 5, 2015

Related U.S. Application Data

(63) Continuation of application No. 12/512,532, filed on Jul. 30, 2009, now Pat. No. 8,915,890.

(51) Int. Cl.
| | |
|---|---|
| *A61M 5/34* | (2006.01) |
| *A61M 5/50* | (2006.01) |
| *A61M 5/32* | (2006.01) |

(52) U.S. Cl.
CPC .............. *A61M 5/344* (2013.01); *A61M 5/32* (2013.01); *A61M 5/34* (2013.01); *A61M 5/5086* (2013.01);
(Continued)

(58) Field of Classification Search
CPC ...... A61M 5/3293; A61M 5/34; A61M 5/344; A61M 5/345; A61M 5/346; A61M 5/348;
(Continued)

(56) References Cited

U.S. PATENT DOCUMENTS

| | | | |
|---|---|---|---|
| 791,802 A | 6/1905 | De Lisle | |
| 1,012,700 A | 12/1911 | Payne | |

(Continued)

FOREIGN PATENT DOCUMENTS

| | | |
|---|---|---|
| DE | 8805331 | 9/1988 |
| EP | 0696460 | 2/1996 |

(Continued)

OTHER PUBLICATIONS

Final Office Action in U.S. Appl. No. 12/512,532, dated Jul. 20, 2012, 15 pages.

(Continued)

*Primary Examiner* — Kami A Bosworth
(74) *Attorney, Agent, or Firm* — Servilla Whitney LLC

(57) ABSTRACT

Medical device assemblies having a connection mechanism for securely connecting a hub to fluid storage containers in a luer slip relationship are described. An exemplary medical device includes a hub forming a cavity, a second indicating element disposed within the cavity that engages the hub. Additional features of the medical device include a second indicating element contoured to form a line contact with the hub. In a specific configuration, the hub includes a first indicating element attached to the hub and extending proximally into the cavity having a protrusion. In a more specific configuration, the medical device includes a fluid storage container that has an indication system for visually indicating optimal fluid-tight engagement of the hub and the fluid storage container.

16 Claims, 21 Drawing Sheets

(52) U.S. Cl.
CPC ..... *A61M 5/3293* (2013.01); *A61M 2205/583* (2013.01); *Y10S 604/905* (2013.01)

(58) Field of Classification Search
CPC ............ A61M 5/5086; A61M 2205/58; A61M 2205/581; A61M 2205/582; A61M 2205/583; A61M 2205/584; A61M 2039/1044; Y10S 604/905
See application file for complete search history.

(56) References Cited

U.S. PATENT DOCUMENTS

| | | |
|---|---|---|
| 1,522,198 A | 1/1925 | Marcy |
| 1,524,242 A | 1/1925 | Hein |
| 1,591,762 A | 7/1926 | Haines |
| 1,683,349 A | 9/1928 | Hein |
| 1,683,350 A | 9/1928 | Hein |
| 2,020,111 A | 11/1935 | Eisele |
| 2,034,294 A | 3/1936 | Hein |
| 2,088,338 A | 7/1937 | Popper et al. |
| 2,577,556 A | 12/1951 | Williams |
| 2,699,777 A | 1/1955 | Voorhorst |
| 2,764,978 A | 10/1956 | Everett |
| 2,806,473 A | 9/1957 | Lingley |
| 2,828,743 A | 4/1958 | Ashkenaz |
| 2,834,346 A | 5/1958 | Adams |
| 2,855,927 A | 10/1958 | Henderson |
| 2,902,995 A | 9/1959 | Loper |
| 3,043,304 A | 7/1962 | Higgins |
| 3,450,135 A | 6/1969 | Sarnoff |
| 3,469,581 A | 9/1969 | Burke |
| 3,472,227 A | 10/1969 | Burke |
| 3,491,757 A | 1/1970 | Arce |
| 3,527,217 A | 9/1970 | Gettig |
| 3,633,944 A | 1/1972 | Hamburg |
| 3,977,403 A | 8/1976 | Patel |
| 3,994,295 A | 11/1976 | Wulff |
| 4,040,421 A | 8/1977 | Young |
| 4,187,848 A | 2/1980 | Taylor |
| 4,281,653 A | 8/1981 | Barta et al. |
| 4,369,781 A | 1/1983 | Gilson et al. |
| 4,430,080 A | 2/1984 | Pasquini et al. |
| 4,457,749 A | 7/1984 | Bellotti et al. |
| 4,490,142 A | 12/1984 | Silvern |
| 4,547,194 A | 10/1985 | Moorehead |
| 4,589,871 A | 5/1986 | Imbert |
| 4,613,329 A | 9/1986 | Bodicky |
| 4,664,656 A | 5/1987 | Taddei |
| 4,675,020 A | 6/1987 | McPhee |
| 4,676,530 A | 6/1987 | Nordgren |
| 4,723,945 A | 2/1988 | Theiling |
| 4,747,839 A | 5/1988 | Tarello et al. |
| 4,822,343 A | 4/1989 | Beiser |
| 4,842,592 A | 6/1989 | Caggiani et al. |
| 4,927,417 A | 5/1990 | Moncada et al. |
| 4,929,243 A | 5/1990 | Koch et al. |
| 4,984,580 A | 1/1991 | Wanamaker |
| 5,026,355 A | 6/1991 | Sweeney et al. |
| 5,047,021 A | 9/1991 | Utterberg |
| 5,053,015 A | 10/1991 | Gross |
| 5,066,287 A | 11/1991 | Ryan |
| 5,069,225 A | 12/1991 | Okamura |
| 5,135,514 A | 8/1992 | Kimber |
| 5,188,620 A | 2/1993 | Jepson et al. |
| 5,209,740 A | 5/1993 | Bryant et al. |
| 5,221,272 A | 6/1993 | Proni |
| 5,257,832 A | 11/1993 | Phan et al. |
| 5,312,377 A | 5/1994 | Dalton |
| 5,348,544 A | 9/1994 | Sweeney et al. |
| 5,405,330 A | 4/1995 | Zunitch et al. |
| 5,405,340 A | 4/1995 | Fageol et al. |
| 5,456,675 A | 10/1995 | Wolbring et al. |
| 5,458,577 A | 10/1995 | Kishigami |
| 5,458,580 A | 10/1995 | Hajishoreh |
| 5,466,223 A | 11/1995 | Bressler et al. |
| 5,535,771 A | 7/1996 | Purdy et al. |
| 5,584,817 A * | 12/1996 | van den Haak ...... A61M 5/322 604/110 |
| 5,611,786 A | 3/1997 | Kirchhofer et al. |
| 5,616,136 A | 4/1997 | Shillington |
| 5,637,101 A | 6/1997 | Shillington |
| 5,681,295 A | 10/1997 | Gyure et al. |
| 5,693,028 A | 12/1997 | Shillington |
| 5,713,876 A | 2/1998 | Bogert et al. |
| 5,733,265 A | 3/1998 | Bachman et al. |
| 5,772,643 A | 6/1998 | Howell et al. |
| 5,810,768 A | 9/1998 | Lopez |
| 5,810,782 A | 9/1998 | Saito |
| 5,830,189 A | 11/1998 | Chang |
| 5,836,919 A | 11/1998 | Skurka et al. |
| 5,851,201 A | 12/1998 | Ritger et al. |
| 5,855,568 A | 1/1999 | Battiato et al. |
| 5,913,846 A | 6/1999 | Szabo |
| 5,919,169 A | 7/1999 | Grams et al. |
| 5,925,020 A | 7/1999 | Nestell |
| 5,968,020 A | 10/1999 | Saito |
| 6,063,068 A | 5/2000 | Fowles |
| 6,132,402 A | 10/2000 | Tessmann et al. |
| 6,217,560 B1 | 4/2001 | Ritger et al. |
| 6,224,576 B1 | 5/2001 | Thorne et al. |
| 6,436,076 B1 | 8/2002 | Hsu |
| 6,629,774 B1 | 10/2003 | Gruendeman |
| 6,629,960 B2 | 10/2003 | Fontayne |
| 6,706,022 B1 | 3/2004 | Leinsing et al. |
| 6,709,428 B2 | 3/2004 | Sagstetter |
| 6,971,390 B1 | 12/2005 | Vasek et al. |
| 7,080,672 B2 | 7/2006 | Fournie et al. |
| 7,115,114 B2 | 10/2006 | Caizza |
| 7,217,258 B2 | 5/2007 | Caizza |
| 8,915,890 B2 | 12/2014 | Lum |
| 2002/0138045 A1 | 9/2002 | Moen |
| 2004/0220533 A1 | 11/2004 | Caizza et al. |
| 2007/0173776 A1 | 7/2007 | Caizza et al. |
| 2007/0185461 A1 | 8/2007 | Caizza et al. |
| 2011/0028909 A1 | 2/2011 | Lum |

FOREIGN PATENT DOCUMENTS

| | | |
|---|---|---|
| EP | 1254677 | 12/2005 |
| EP | 2459256 | 6/2012 |
| FR | 567078 | 2/1924 |
| GB | 1574187 | 9/1980 |
| JP | S52-83294 | 12/1977 |
| JP | 58-005891 | 1/1979 |
| JP | 59-2750 | 1/1984 |
| JP | 3031444 | 3/1991 |
| JP | 07-31679 | 3/1995 |
| JP | 07-303697 | 11/1995 |
| JP | 08-000732 | 1/1996 |
| JP | 08-57058 | 3/1996 |
| JP | 10-113392 | 5/1998 |
| JP | 11-507275 | 6/1999 |
| JP | 2000-116781 | 4/2000 |
| JP | 2000-116796 | 4/2000 |
| JP | 2002-515311 | 5/2002 |
| JP | 2003-505158 | 2/2003 |
| JP | 2003-88587 | 3/2003 |
| WO | WO-91/03269 | 3/1991 |
| WO | 2011/014444 A1 | 2/2011 |

OTHER PUBLICATIONS

PCT International Preliminary Report on Patentability and Written Opinion in PCT/US2010/043200, dated Jan. 31, 2012, 8 pages.
PCT International Search Report in PCT/US2010/043200, dated Oct. 5, 2010, 3 pages.
Non-Final Office Action in U.S. Appl. No. 12/512,532, dated Feb. 16, 2012, 18 pages.
Non-Final Office Action in U.S. Appl. No. 12/512,532, dated Jun. 3, 2014, 10 pages.

* cited by examiner

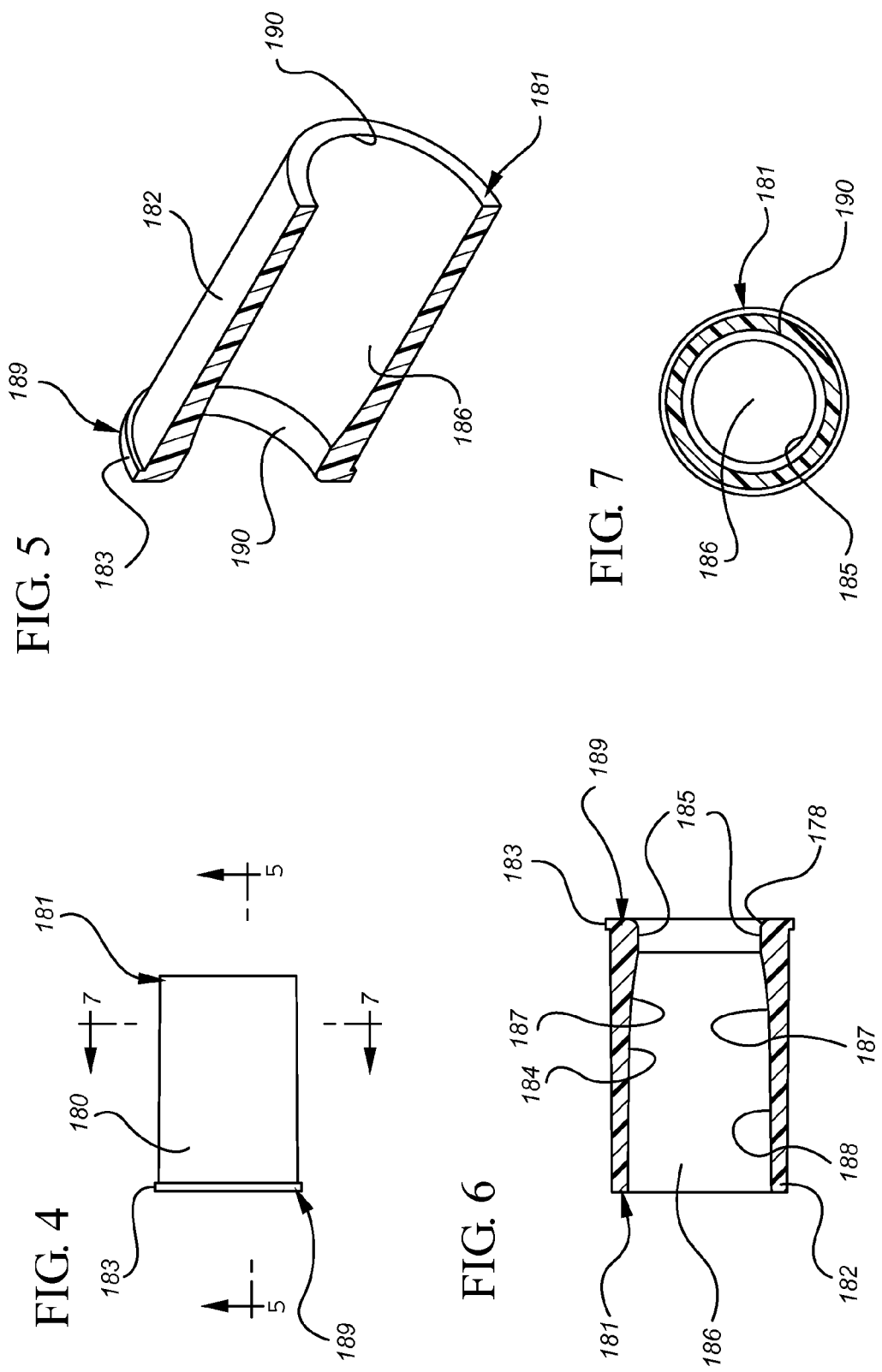

MEDICAL DEVICE ASSEMBLY

CROSS-REFERENCE TO RELATED APPLICATIONS

This application is a continuation of U.S. patent application Ser. No. 12/512,532, filed on Jul. 30, 2009, now U.S. Pat. No. 8,915,890, issued on Dec. 23, 2014, the disclosures of which are incorporated herein by reference in their entirety.

TECHNICAL FIELD

Aspects of the present invention relate to medical devices having a luer slip mechanism for connection to a fluid storage container.

BACKGROUND

Fluid storage containers, such as syringes, having a luer fitting or connection are often assembled with hubs or luer fittings. Two common mechanisms used to connect the hubs to the syringes include the "luer lock" and "luer slip" mechanisms.

The luer lock mechanism generally includes a fluid storage container with a male fitting in co-axial relation with an internally threaded collar. A cooperating hub or female luer lock fittings have external lugs for engaging the internally threaded collar of the male conical fitting, upon application of a twisting force or torque force to the hub.

The luer slip fitting generally includes a fluid storage container with a male fitting without a threaded collar. Cooperating hubs or female luer slip fittings typically have an internal surface which slides over the external surface of the male fitting. The hub is attached to the male fitting in a friction fit or interference fit relationship. To attach the hub to the male fitting, the user must apply enough force when sliding the hub over the male fitting to create a fluid-tight relationship between the hub and male fitting. Failure to securely connect the hub and medical device can result in "pop offs," where the unsecured hub detaches from the male fitting during use.

A medical device with a connection mechanism for securely connecting a hub to fluid storage containers in a luer slip relationship, as defined herein, presents a viable solution to these issues. In addition, there is a need for a mechanism that indicates such secure connection between a hub and fluid container.

SUMMARY

A first aspect of the present invention pertains to medical devices for use with fluid storage containers. Medical devices have structure that forms line contact interactions between a first indicating element of the hub and a second indicating element of the hub when the fluid storage container is securely connected to the hub. As used herein, the term "line contact" shall include contact between two surfaces at two or more points, wherein one or both of the surfaces are compressible and/or non-compressible. As used herein, the term "surface contact" or "point contact" shall include contact between two surfaces at a single point, wherein one or both of the surfaces are compressible and/or non-compressible. In one or more embodiments, the medical device includes a hub with a distal end with an opening, an open proximal end and a sidewall extending from the distal end to the proximal end forming a cavity. The medical device further includes a first indicating element attached to the distal end of the hub extending into the cavity and a second indicating element disposed within the cavity. In one or more embodiments, one of either the first indicating element or the second indicating element is flexible.

In one or more embodiments, the opening of the hub at the distal end is in fluid communication with the cavity. The hub may optionally include a needle cannula attached to its distal end and extending in the distal direction. The needle cannula used with one or more embodiments, includes a proximal end, a distal end and a lumen therethrough in fluid communication with the cavity. Alternative embodiments of the hub may include a safety cap covering the needle cannula. In a specific embodiment, the hub may include a coaxial wall extending from the distal end of the hub that forms a channel between the coaxial wall and the sidewall of the hub for receiving the safety cap.

The first indicating element includes a distal end attached to the distal end of the hub and a proximal end that extends into the cavity of the hub. In one or more embodiments, the distal end of the first indicating element surrounds the opening in the distal end of the hub. The first indicating element of one or more embodiments forms a recess with the sidewall of the hub. The first indicating element may also include an outwardly radially extending protrusion. In one or more embodiments the protrusion is disposed on the outside surface of the first indicating element and extends into the recess formed between the first indicating element and the sidewall of the hub.

The second indicating element of one or more embodiments includes an open proximal end, an open distal end and a body extending from the open proximal end to the open distal end. The body includes an inside surface that defines a hollow interior. The body of one or more embodiments of the second indicating element may be hollow and cylindrical.

In one or more embodiments, the hollow interior is sized and shaped to envelope or receive the first indicating element. In a more specific embodiment, the hollow interior allows the body of the second indicating element to enter the recess formed between the first indicating element and the sidewall of the hub. The body of the second indicating element enters the recess upon application of a distally directed force on the second indicating element. In one or more embodiments, the protrusion of the first indicating element prevents the body from entering the recess until a pre-determined distally-directed force is applied to the second indicating element. In a specific embodiment, the protrusion is shaped and/or adapted to advance proximally into the hollow interior of the second indicating element as the body of the second indicating element enters the recess.

In accordance with one or more embodiments the inside surface of the second indicating element or the cross-sectional width formed by the inside surface is contoured to form a line contact interaction with the first indicating element upon application of a force on the second indicating element in the distal direction. As used herein, the term "cross-sectional width" shall include the longest distance between two points on the circumference or edge of the cross-section of an object having a circular and non-circular cross-section. The two points may be located on the interior or exterior surface circumference or edge of the cross-section of the object. It should be recognized that "cross-sectional width" of objects having a circular cross-section may be referred to as the "diameter" of the object. The terms "cross-sectional width" and "diameter" may be used interchangeably for objects having a circular cross-section.

In a specific embodiment, the inside surface includes a first diameter portion adjacent to the open distal end of the second indicating element. The inside surface may also include a second diameter portion having an axial length extending from the first diameter portion to the open proximal end. In one or more embodiments, the diameter of the inside surface increases along the second diameter portion from the first diameter portion toward the open proximal end of the second indicating element.

In accordance with one or more embodiments, the second indicating element includes an inside surface defining a cross-sectional width. The inside surface includes a tapered portion adjacent to the open distal end of the body, a ramped portion distally adjacent to the tapered portion, an enlarged portion adjacent the open proximal end of the body. In one or more embodiments, the ramped portion has an axial length extending from the tapered diameter portion toward the enlarged portion. In a specific embodiment, the cross-sectional width of the inside surface increases along the axial length of the ramped portion from the tapered portion toward the enlarged portion. The second indicating element of one or more embodiments is adapted to slide distally over the first indicating element, as will be described herein. In a specific embodiment, the ramped portion of the inside surface of the second indicating element forms a line contact interaction with the first indicating element as the second indicating element receives the first indicating element. In a more specific embodiment, the axial length of the ramped portion may be reduced to provide tactile feedback upon fluid-tight engagement of a fluid storage container and a hub.

The second indicating element with a tapered portion may be utilized with a first indicating element having a protrusion shaped and/or adapted to slide proximally past the tapered portion upon application of a pre-determined force on the second indicating element in a distal direction relative to the first indicating element. Alternatively, the protrusion may be shaped and/or adapted to prevent the second indicating element from engaging the first indicating element or sliding distally over the first indicating element until a pre-determined force is applied to the second indicating element in a proximal direction relative to the first indicating element.

The open distal end of one or more embodiments of the second indicating element includes a continuous or solid perimeter. In one or more embodiments, the continuous or solid perimeter has a circular form that is maintained upon application of a distally directed force on the second indicating element until the hub and the fluid container are in fluid-tight engagement.

One or more embodiments of the medical devices described herein may incorporate means for indicating application of a force on the hub sufficient to result in fluid-tight engagement of the hub with a fluid storage device. In accordance with one or more embodiments, the means forms at least two contact points with the hub. For example, the hub may include a first indicating element at its distal end extending proximally into the cavity from the opening and the means forms at least two contact points with the second indicating element during application of the force on the hub. In one or more embodiments the first indicating element may also include a radially extending protrusion and the means for indicating comprises a hollow cylindrical body having a proximal end, a distal end and an inside surface extending from the proximal end to the distal end that has a diameter that increases from the distal end to the proximal end. In a specific embodiment, the hollow cylindrical body has a circular cross-section that maintains its circular shape during application of the required force on the hub. In a more specific embodiment, the means for indicating produces tactile feedback upon fluid-tight engagement of the hub and the fluid storage device.

A second aspect of the present invention pertains to a feature that includes a visual indicator. The visual indicator may be used with one or more embodiments of the medical device described herein. The visual indicator is disposed on a fluid storage device, for example, adjacent to the opening of the fluid storage device. In one or more embodiments, the fluid storage device includes a syringe barrel with a luer tip and the visual indicator is disposed on the tip. In alternative embodiments, the fluid storage device includes a male luer connector and the visual indicator is disposed on the male luer connector. The visual indicator is disposed at a location on the tip such that it is fully visible prior to fluid-tight engagement of the fluid-transfer device and the medical device or hub of the medical device. The first predefined portion of the visual indicator is also visible when the connection between the fluid storage device and the medical device is under tightened. In accordance with one or more embodiments, a second predefined portion which is less than the first predefined portion of the visual indicator is visible upon optimal tightening and/or fluid-tight engagement of the fluid storage device and the hub. In a specific embodiment, the visual indicator is not visible when the connection between the fluid storage device and the hub is over tightened. The fluid storage devices described herein may be utilized with one or more embodiments of the medical devices described herein regardless of whether the medical device utilizes the visual indication feature.

BRIEF DESCRIPTION OF THE DRAWINGS

FIG. 4 is an enlarged view of the second indicating element shown in FIG. 2;

FIG. 5 is a perspective cross-sectional view of the second indicating element shown in FIG. 4 taken along line 5-5;

FIG. 6 is an enlarged sectional view of the second indicating element shown in FIG. 3;

FIG. 7 is a cross-sectional view of the second indicating element shown in FIG. 4 taken along line 7-7;

DETAILED DESCRIPTION

Figure 1:
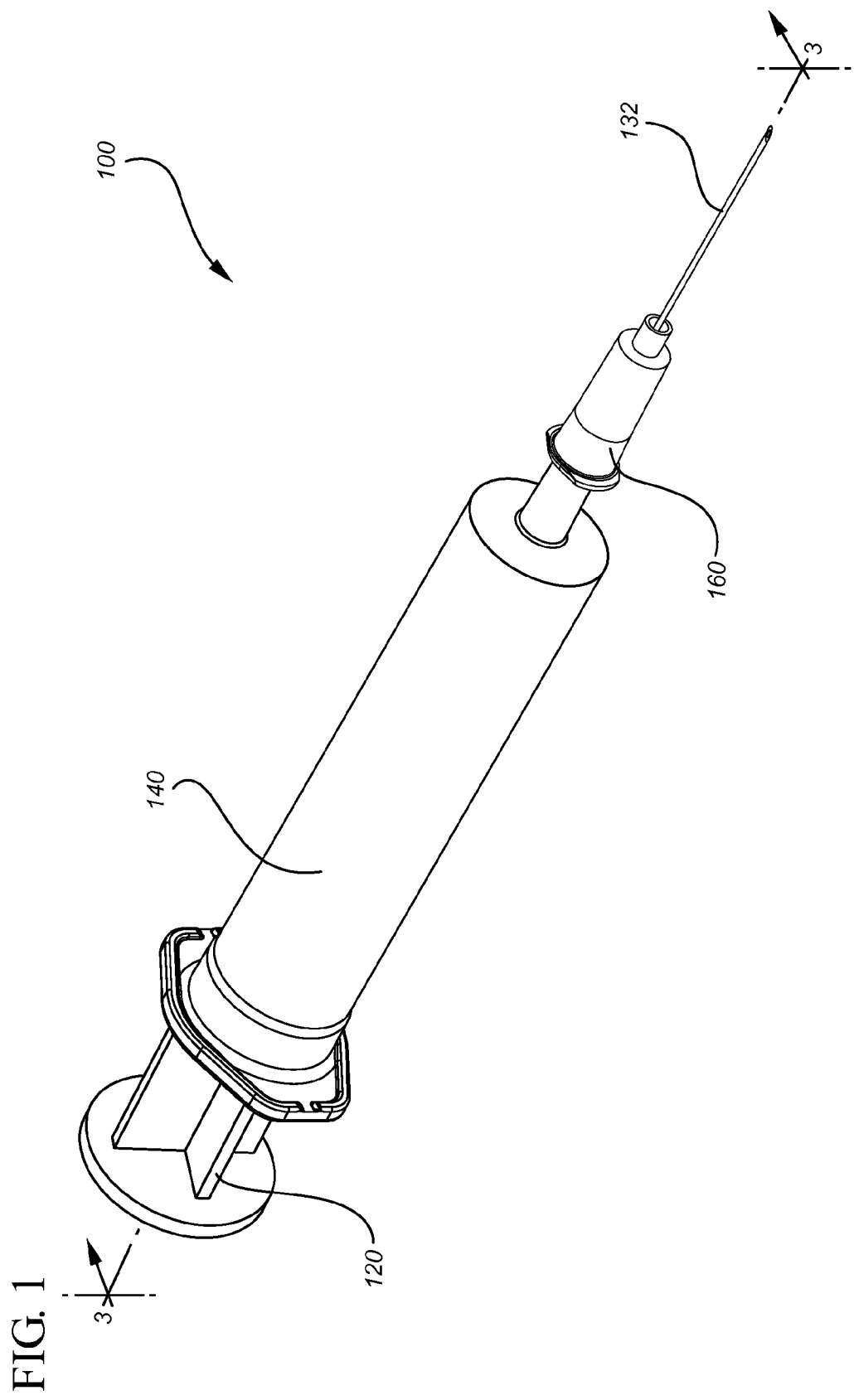
FIG. 1 illustrates a medical device assembly according to one or more embodiments of the invention shown attached to a fluid storage container.
Figure 2:
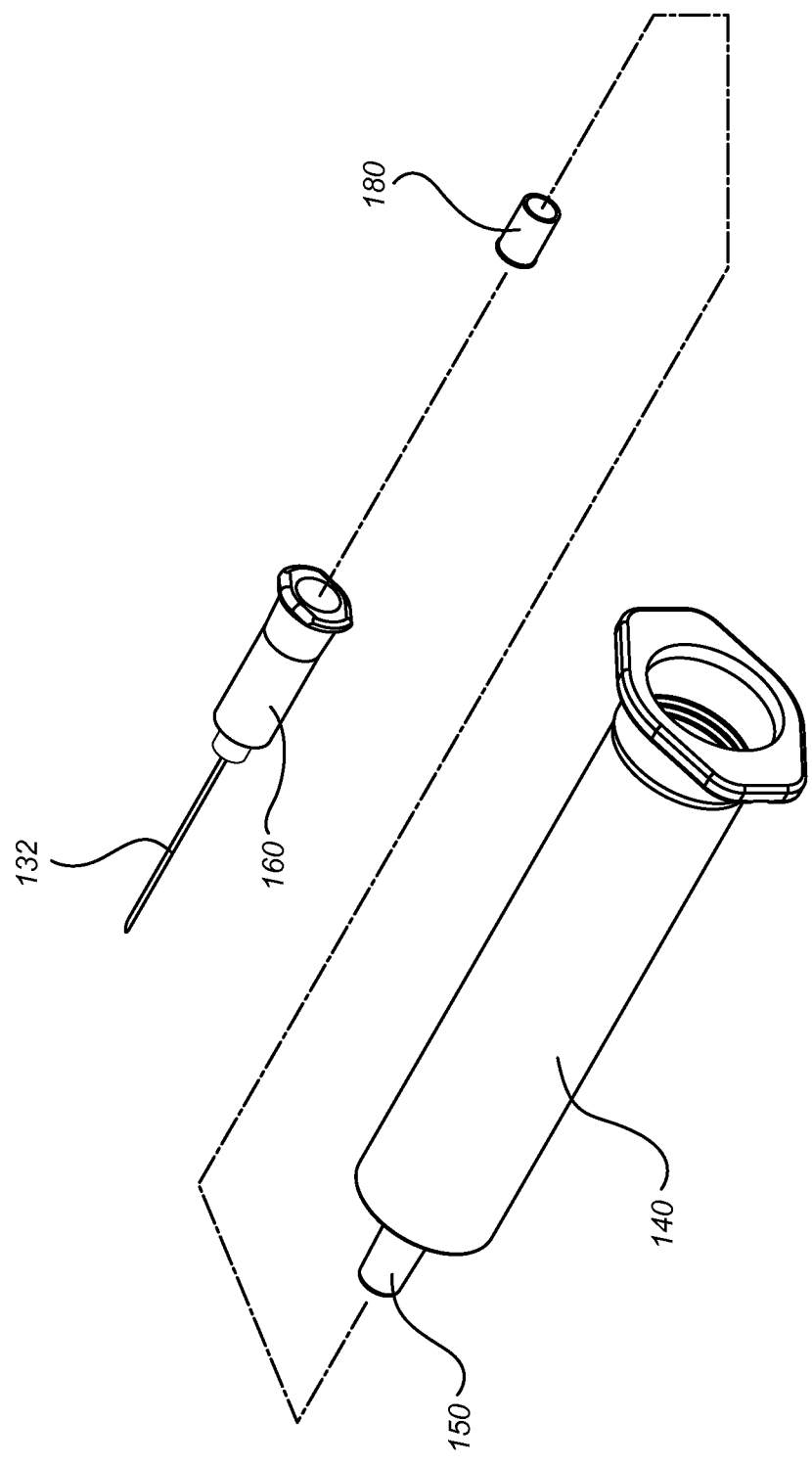
FIG. 2 shows an exploded view of the assembly of FIG. 1.
Figure 3:
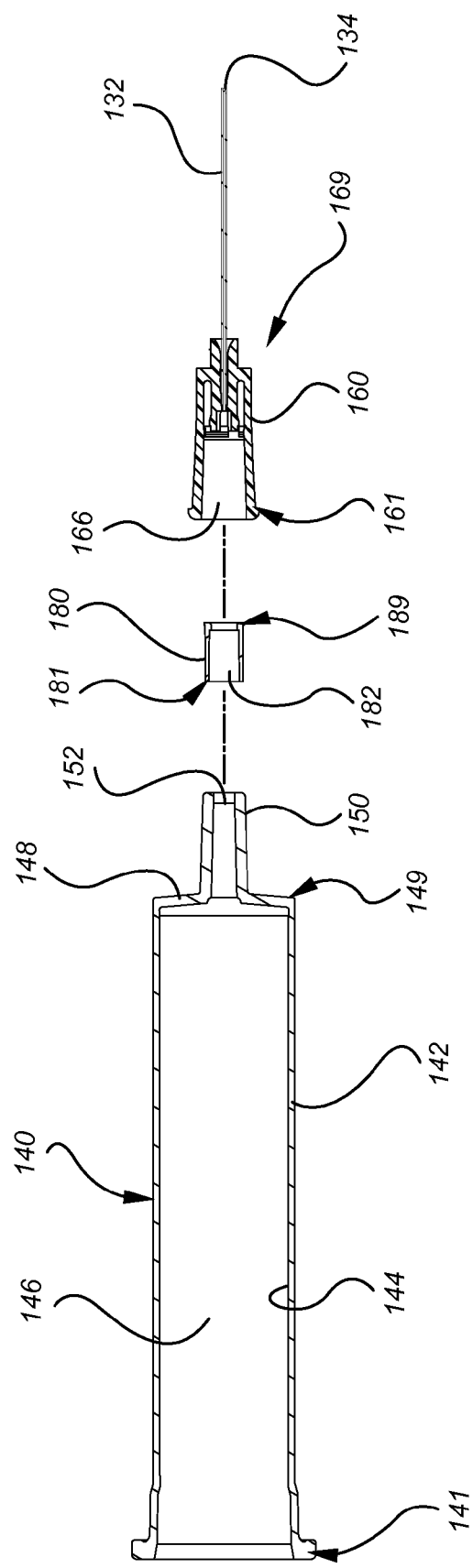
FIG. 3 is an exploded cross-sectional view of the hub, second indicating element and fluid storage container shown in FIG. 1 taken along line 3-3.

Before describing several exemplary embodiments of the invention, it is to be understood that the invention is not limited to the details of construction or process steps set forth in the following description. The invention is capable of other embodiments and of being practiced or being carried out in various ways.

One aspect of the present invention provides for a medical device assembly that may be connected or attached in fluid-tight engagement with a fluid storage container. The medical device assembly of one or more embodiments may utilize a first indicating element and/or a second indicating element as a means for indicating fluid-tight engagement with a fluid storage container. One or more embodiments of the medical device assembly include a hub and means for indicating application of a force on the hub sufficient to result in fluid tight engagement with a fluid storage container. The means for indicating may be utilized during engagement of the medical device assembly and the fluid storage container in a luer slip configuration. The embodiments of the medical device assemblies described herein may be used with an optional needle cannula and/or an optional needle tip cap.

FIGS. 1-21 illustrate a medical device assembly according to one or more embodiments. It will be understood that medical device assembly may be used with fluid storage containers such as syringe barrels, needleless IV sets, or other devices that can be used to store and/or transfer medication or other liquid. In one or more embodiments, the fluid storage container includes an opening providing access to the contents of the container. The opening may include a male luer fitting or may be otherwise configured for use with the medical device assembly.

FIGS. 1-21 illustrate a medical device assembly according to the invention, including a hub 160 having means for indicating application of a force on the hub sufficient to result in fluid tight engagement with a fluid storage container 140. In one or more embodiments, the means for indicating application of such a force forms at least two contact points with the hub during application of the force. In one or more embodiments, the means for indicating application of such a force includes a first indicating element 170 attached to or integrally formed with the hub and/or a second indicating element 180 disposed within the hub 160.

FIGS. 1-7 show an embodiment of the medical device assembly that includes an optional needle cannula 132 attached to a hub 160. FIG. 1-7 also show an optional fluid storage container 140 in the form of a syringe barrel attached to the hub to form a fluid delivery system 100. In one or more embodiments, the fluid storage container 140 has a sidewall 142 with an inside surface 144 that defines a chamber 146 for holding the contents of the container, which may include medication. The container 140 includes an open proximal end 141 and a distal end 149 and a distal wall 148. The distal wall 148 includes a luer tip 150 having an opening 152 in fluid communication with the chamber 146. The fluid storage container 140 may include a plunger rod 120 inserted into the proximal end 141 of the fluid storage container 140. It is to be understood that the configuration shown is merely exemplary, and the components can be different in shape and size than shown.

Figure 9A:
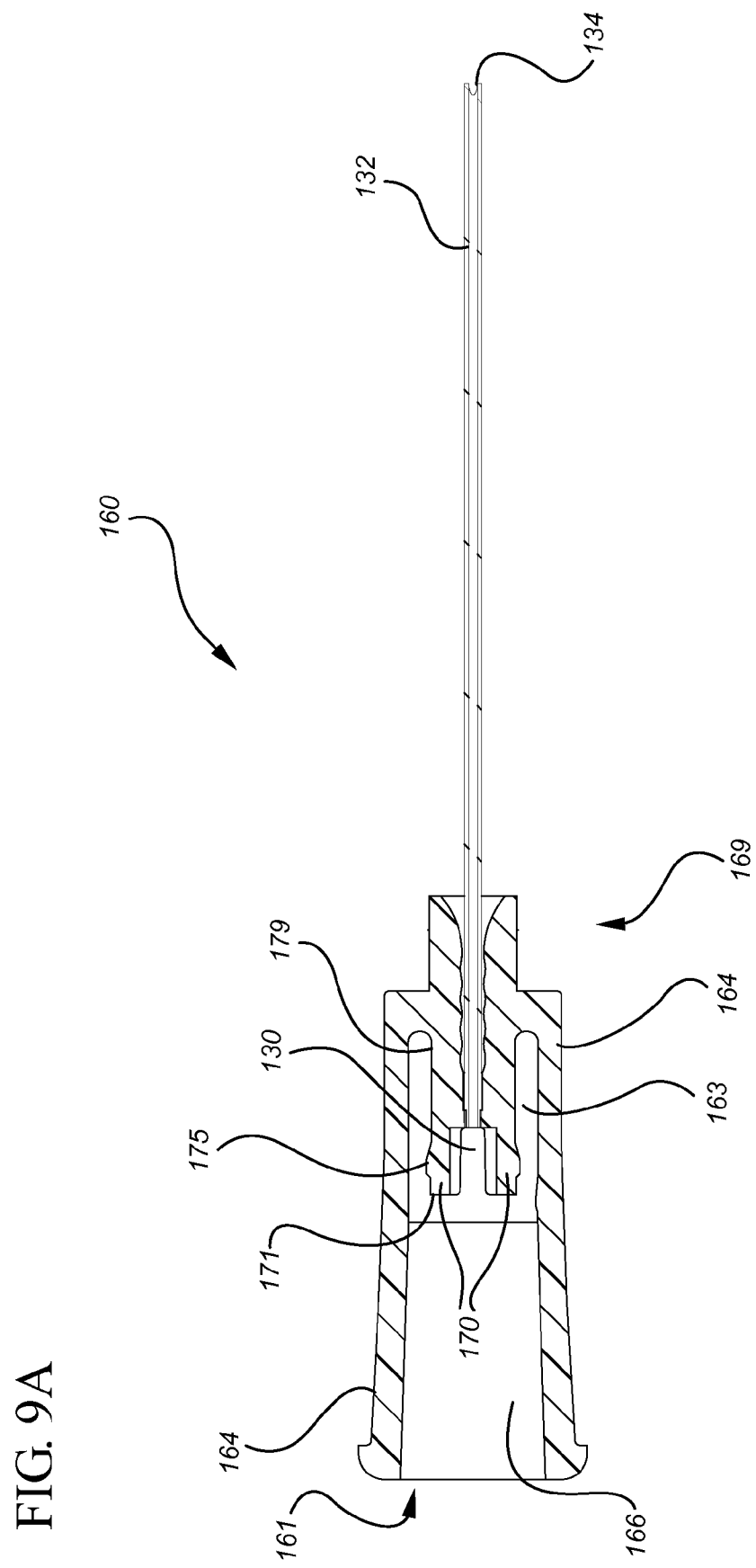
FIG. 9A is an enlarged sectional view of the hub shown in FIG. 3.

The hub 160 shown more clearly in FIG. 9A includes an open proximal end 161 and a distal end 169 that includes the optional needle cannula 132 having a lumen 134 therethrough. The hub 160 includes a sidewall 164 extending from the distal end 169 toward the open proximal end 161 and defining a cavity 166. The distal end 169 includes a passageway 130 therethrough in fluid communication with the lumen 134 of the optional needle cannula 132. As more clearly shown in FIG. 10, a second indicating element 180 is disposed within the cavity 166 of the hub 160.

The distal end 169 of the hub 160 further includes a first indicating element 170 having a distal end 179 attached to the distal end 169 of the hub 160 and a free proximal end 171 extending proximally into the cavity 166. In a specific embodiment, the first indicating element 170 is permanently attached to the distal end 169 of the hub. In a more specific embodiment, the first indicating element 170 is integrally formed with the hub 160. In an alternative embodiment, the first indicating element 170 is a separate component that may be attached or affixed to the distal end 169 of the hub. The first indicating element 170 of one or more embodiments is substantially free of threads and forms an interference fit engagement with the second indicating element 180, as will be more fully described below. The first indicating element 170 forms a recess 163 with the sidewall 164. The recess 163 may extend from the distal end 169 of the hub to the free proximal end 171 of the first indicating element 170. In one or more embodiments, the first indicating element may be in the form of a second sidewall formed coaxially with the sidewall 164 of the hub, forming peripheral recess with the sidewall 164 of the hub. In a specific embodiment, the coaxially formed second sidewall may encircle or surround the passageway 130. In a more specific embodiment, the first indicating element may include a cantilevered beam attached to the distal end 169 of the hub adjacent to the passageway 130 and extending into the cavity 166.

The recess 163 is shaped to receive the second indicating element 180 when the hub is attached to a fluid storage container. The first indicating element 170 includes at least one protrusion 175 extending radially outwardly from the outer surface of the first indicating element 170 into the recess 163. The protrusion 175 may be a single extending portion or may be a ridge formed concentrically around the first indicating element 170. In one or more embodiments, the location of the protrusion may be modified to indicate fluid tight connection with fluid storage containers having different shapes and for use with second indicating elements 180 with different sizes and shapes.

Figure 9B:
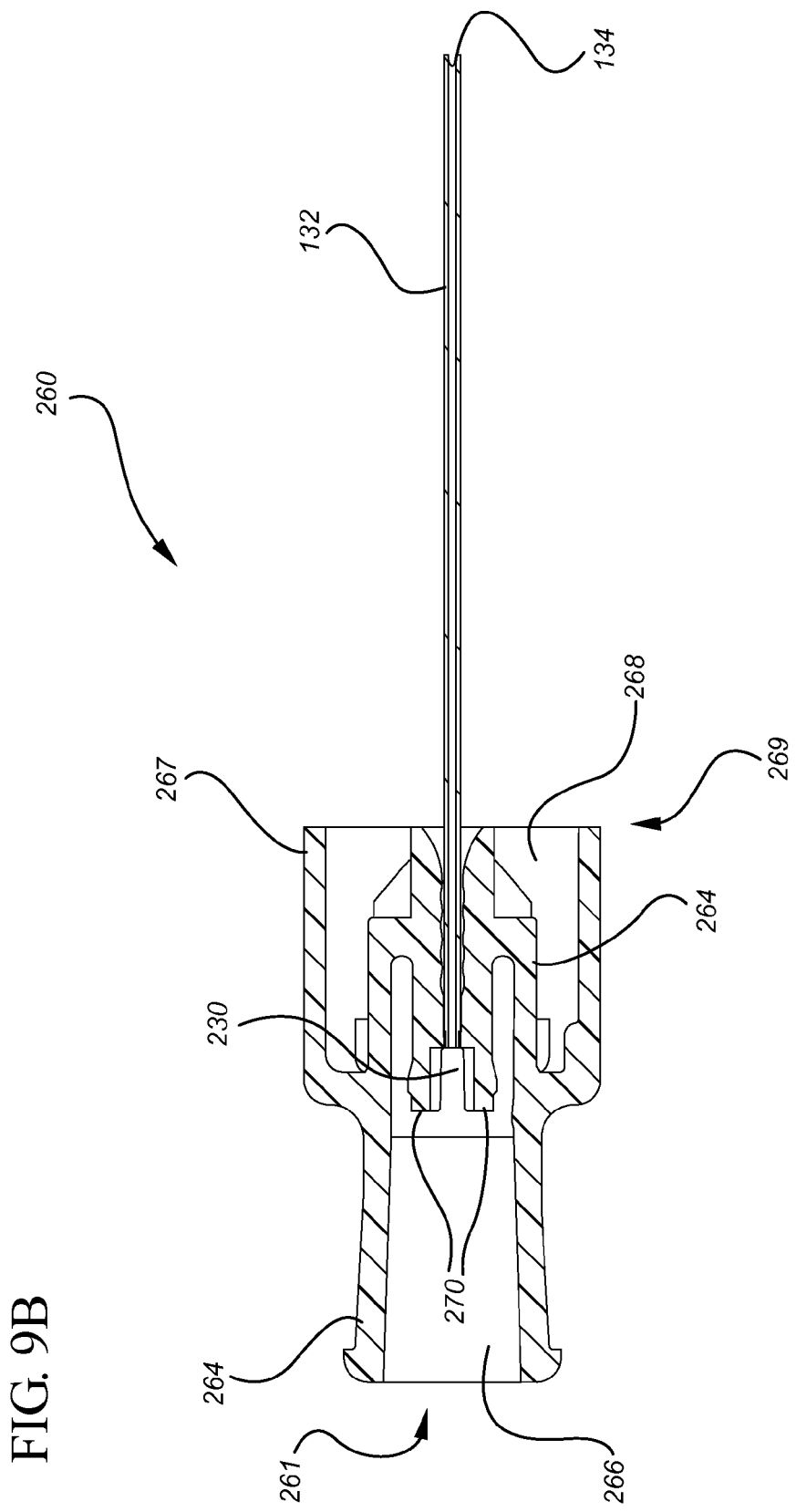
FIG. 9B is an enlarged sectional view of a hub according to an alternative embodiment.
Figure 10:
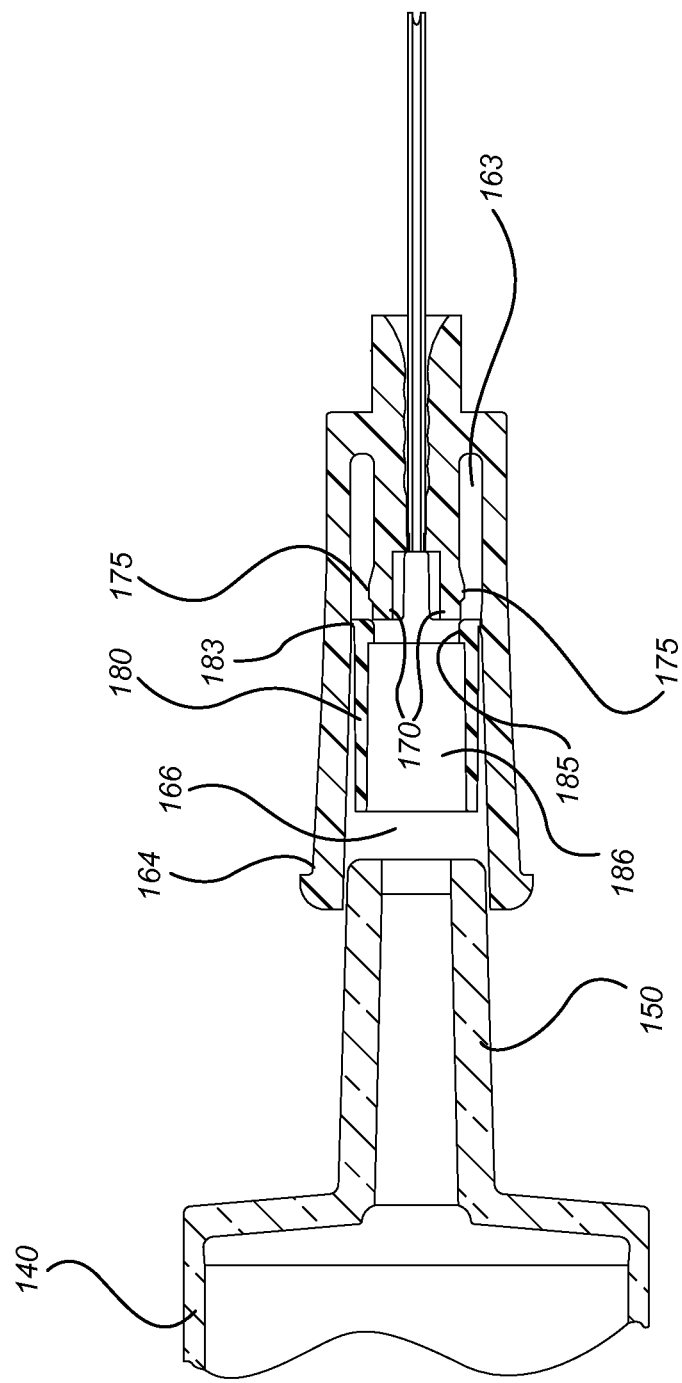
FIG. 10 is a cross-sectional view of the hub, second indicating element and the fluid storage container shown in FIG. 3 partially assembled.
Figure 11:
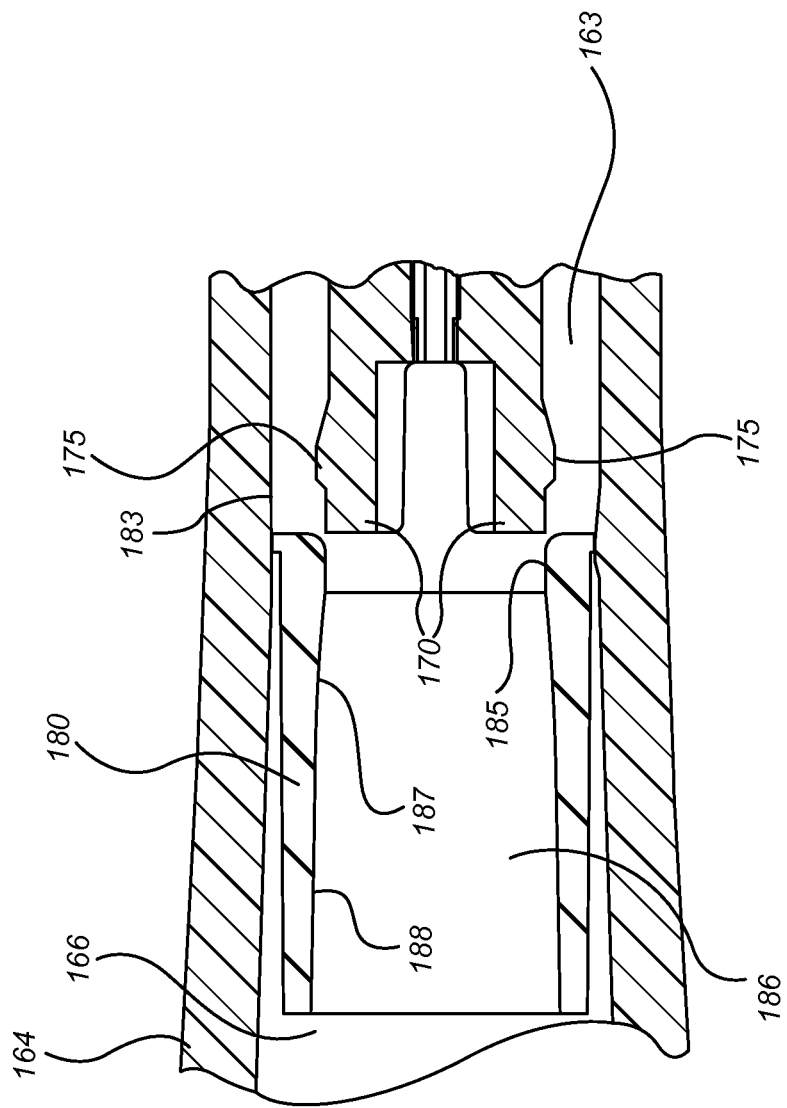
FIG. 11 is an enlarged view of FIG. 10.

In the alternative embodiment shown in FIG. 9B, the medical device of the invention may include a hub 260 with a needle cannula 132 wherein the hub 260 is configured to incorporate one or more components to prevent contamination and accidental sticking and/or to protect the needle cannula 132, such as a needle tip cap (not shown). The hub 260 includes a distal end 269 with a passageway 230 therethrough, an open proximal end 261, and a sidewall 264 extending from the distal end 269 and the proximal end 261 that defines a cavity 266. The hub 260 includes first indicating element 270 for indicating fluid-tight engagement between the hub 260 and a fluid storage container. The hub 260 includes a coaxial wall 267 formed around the sidewall 264 at the distal end 269. The coaxial wall 267 forms a channel 268 for receiving a needle tip cap (not shown).

The needle cannula 132 may be made of various materials known in the art, including metals such as stainless steel, and may be held in the hub 160 or 260 using known manufacturing methods. For example, adhesives may be used to hold the needle. The hub may be manufactured using known methods such as injection molding and may be made of injection moldable plastic such as polypropylene, polyethylene, polycarbonate and combinations thereof. The needle cannula and hub may also be integrally formed of thermoplastic material. The sidewall 164 of the hub may also be shaped to attach to a variety of fluid storage containers.

The shape of the hub may be modified to form an interference fit with a selected fluid storage container in a luer slip configuration. For example, the hub may be shaped to have a frusto-conical shape to form a luer slip configuration with the tip of a fluid storage container (as shown in FIGS. 9-17). The hub may also be shaped to be used with standard luer slip fittings or other luer fittings known in the art. In one or more embodiments, the sidewall 164 of the hub 160 may be free of any threads for engagement with the fluid storage container in a luer lock configuration.

As shown more clearly in FIGS. 10-17, the second indicating element 180 is disposed within the cavity 166 of the hub 160. Referring to FIGS. 4-7, the second indicating element 180 includes an open proximal end 181 and an open distal end 189. The second indicating element 180 also includes a hollow body 182 having an axial length and an inside surface 184 defining a hollow interior 186 extending from the distal end 189 to the proximal end 181. In one or more embodiments, the second indicating element 180 is shaped and positioned to ensure or to facilitate fluid-tight engagement of the hub 160 and a fluid storage container. In a specific embodiment, the second indicating element 180 is positioned within the cavity 166 of the hub 160 so that when the hub 160 is placed over the opening of a fluid storage container, for example, the tip 150 of a fluid storage container 140, the proximal end 181 of the second indicating element 180 abuts the tip 150, while the distal end 189 of the second indicating element 180 is adjacent to and/or contacts the proximal end 171 of the first indicating element 170, as more clearly shown in FIGS. 10-11.

In one or more embodiments, during assembly, the tip 150 is disposed adjacent to the proximal end 181 of the second indicating element 180 and does not enter the hollow interior 186 of the second indicating element 180 during assembly of the fluid storage container 140 and the hub 160. In accordance with one or more embodiments, the second indicating element 180 is shaped and configured to require a user to apply a pre-determined force on the hub 160 in the proximal direction toward the fluid storage container 140 or a pre-determined force on the fluid storage container 140 in the distal direction toward the hub 160 to allow the second indicating element 180 to advance distally over the first indicating element 170 and the protrusion 175 disposed on the outer surface of the first indicating element 170, as shown in FIGS. 10-17. Application of this pre-determined force results in the displacement of the second indicating element 180 within the cavity 166 into the recess 163, thereby indicating the point at which the hub 160 and the tip 150 form a fluid-tight engagement.

In accordance with one or more embodiments, the protrusion 175 is disposed on the outer surface of the first indicating element 170 and may be modified in shape and location to adjust the pre-determined force required to form a fluid-tight engagement between the hub 160 and the tip 150. For example, the height of the protrusion 175 may be increased to increase the total amount of force needed to be applied on the hub 160 and/or the fluid storage container 140 to form a fluid-tight engagement between the hub 160 and the tip 150. The increased height of the protrusion 170 increases resistance to advancement of the second indicating element 180 in the distal direction over the first indicating element 170. This increased resistance indicates to the user that more force is required to form such engagement between the hub 160 and the tip 150. Advancement of the second indicating element 180 into the recess 163 over the first indicating element 170 indicates sufficient force has been applied to the hub 160 and/or fluid storage container 140 to create fluid-tight engagement.

As more clearly shown in FIGS. 4-7, the second indicating element 180 is shaped to fit over the first indicating element 170 of the hub 160. The hollow body 182 of the second indicating element 180 may be elongate and solid. In one or more embodiments, the inside surface 184 of the hollow body 182 adjacent to the distal end 189 and/or the proximal end 181 of the second indicating element 180 includes a solid, continuous or uninterrupted perimeter 190 that defines the open distal end 189 and/or at the open proximal end 181. In a specific embodiment, the inside surface 184 and/or the outside surface of body 182 may be free of internal threads. In one or more embodiments, the inside surface 184 is shaped to form a hollow interior 186 that can envelope the first indicating element 170 as the second indicating element 180 advances distally over the first indicating element 170. It will be understood that the body 182 extending between the open proximal end 181 and the open distal end 189 of the second indicating element 180 need not be solid and may include openings that allow access to the hollow interior 186 from the open distal end 189, open proximal end 181 or along the body 182, however, the solid perimeter 190 formed by the inside surface 184 adjacent to the open distal end 189 and/or the proximal end 181 is continuous.

The second indicating element 180 is disposed within the cavity 166 of the hub as a separate piece and is not attached or connected to the hub before engagement of the hub to a fluid storage container. In one specific embodiment, the second indicating element 180 may be shaped such that it fits inside the cavity 166 of the hub 160. In a more specific embodiment, the second indicating element 180 may be shaped so it is slideable and/or movable within the cavity 166 of the hub 160. In a more specific embodiment, the second indicating element 180 may be shaped so that it is not rotatable in any direction within the cavity 166 of the hub 160. In an even more specific embodiment, the second indicating element 180 is shaped to allow rotation only around the axis extending from the open distal end 189 and the open proximal end 181.

In one or more embodiments, the outside surface of body 182 has a cross-sectional width that permits the second indicating element 180 to fit within the cavity 166 of the hub

160 and the inside surface 184 at the perimeter has a cross-sectional width that permits the second indicating element 180 to slide distally over the first indicating element 170. In a more specific embodiment, the body 182 has a thickness that allows the second indicating element 180 to advance distally within the recess 163 of the hub 160. The body 182 shown more clearly in FIGS. 4-7 forms a cylinder having a solid circular cross-section along its entire length and includes a continuous solid perimeter 190 at the distal end 189 and the proximal end 181.

It will be understood that the first and second indicating elements may have cross-sections of any shape. In one or more embodiments, the first and/or second indicating element may have a cross-section such that the inside surface of the first and/or second indicating element forms a non-circular shape and the outside surface of the first and/or second indicating element forms a circular shape. In a specific embodiment, the first and/or second indicating element may have a cross-section such that the inside surface forms a circular shape and the outside surface forms a non-circular shape. In embodiments wherein the first and/or second indicating elements have a non-circular cross-section, it will be understood that the medical device assembly may include a means to control orientation of the second indicating element with respect to the first indicating element.

In a more specific embodiment, the outside surface of the body 182 includes an outwardly radially extending lip 183 or projection disposed at one or more points along the length of the outside surface of the body 182. The lip 183 may be disposed near the distal end 181 and/or proximal end 189 of the second indicating element 180. Alternative embodiments may include a second indicating element 180 may include a plurality of lips disposed along the outside surface of the body 182. The lip 183 may be a single protruding point extending outwardly radially from the outside surface of the body 182 or may be peripherally formed around the outside surface of the body 182, as shown in FIGS. 4-7.

In one or more embodiments, the lip 183 increases the thickness of the body 182. In a specific embodiment, the cross-sectional width of the second indicating element 180 at lip is greater than the cross-sectional width of the second indicating element 180 at the exterior surface of the second indicating element 180 at remaining portions of the body 182. As more clearly shown in the embodiment of FIG. 10, the increased cross-sectional width formed by the lip 183 forms a interference or friction fit interaction with the sidewall 164 of the hub 160 so that the second indicating element 180 is retained within the cavity 166 of the hub 160 before engagement of the medical device assembly and a fluid storage container, when forming a fluid delivery system 100.

In one or more embodiments, the inside surface 184 has a cross-sectional width, which is measured at the inside surface 184, that forms an interference fit with the outside surface of the first indicating element 170. As will be described in greater detail, the inside surface 184 of one or more embodiments of the second indicating element 180 defines a gradually tapered cross-sectional width that forms a narrowed portion at one or more points along the length of the inside surface 184. More specifically, the inside surface 184 may be shaped to include a first cross-sectional region defining the narrowest cross-sectional width. In a more specific embodiment, the inside surface 184 may be shaped to include a second cross-sectional region that defines a cross-sectional width measured at the inside surface 184 that is greater than the cross-sectional width at the first cross-sectional region that extends distally and/or proximally from the first cross-sectional region. In one or more embodiments, the second cross-sectional region may include a cross-sectional width that increases as it extends distally and/or proximally from the first cross-sectional region. In alternative embodiments, the inside surface 184 may be shaped to include a third cross-sectional region that has a cross-sectional width measured at the inside surface 184 that is greater than the cross-sectional width of the first and second cross-sectional regions. The third cross-sectional region may be disposed adjacent to the proximal end 181 and/or the distal end 189 of the second indicating element 180. In one or more embodiments, the third cross-sectional region may have a cross-sectional width that increases or decreases along its length. The third cross-sectional region may be disposed adjacent to the second cross-sectional region and the proximal end 181 and/or distal end 189 of the second indicating element 180.

In the embodiment shown in FIGS. 4-7, the second indicating element 180 includes a circular cross-section and has an inside surface 184 defining a first diameter region 185 that may have a narrowed cross-sectional width or diameter measured along the circumference of the inside surface at one or more points along the axial length of the body 182. In one or more embodiments, the first diameter region 185 is a tapered portion that has a cross-sectional width that gradually decreases, with respect to the cross-sectional width defined by the remaining portions of the inside surface 184 of the second indicating element 180. The second indicating element 180 may also include a second diameter region 187 at one or more points along the axial length of the inside surface 184 that extends from the first diameter region 185 toward the distal end 189 and/or the proximal end 181 of the second indicating element 180. In one or more embodiments, the inside surface 184 includes a first diameter region 185 adjacent the open distal end 189 of the second indicating element 180 and a second diameter region 187 having an axial length extending from the first diameter region 185 to the open proximal end 181 such that the diameter of the inside surface 184 increases along the second diameter region 187 from the first diameter region 185 toward the proximal end 181. In such embodiments, the second diameter region 180 forms a ramp or ramped portion having a proximally increasing diameter measured at the inside surface 184. In a specific embodiment, the first diameter region 185 is disposed adjacent to the proximal end 181 of the second indicating element 180 and the second diameter region 187 extends distally toward the distal end 189 of the second indicating element 180.

The inside surface 184 of the second indicating element 180 may also include a third diameter region 188 that has a diameter greater than the diameter at the first diameter region 185 and the diameter at the second diameter region 187. In one or more embodiments, the third diameter region 188 has a diameter that is constant along its entire length. In a specific embodiment, the third diameter region 188 has a diameter that increases along its length in the proximal or distal direction.

In embodiments which utilize a first diameter region 185, a second diameter region 187 and a third diameter region 188, the second diameter region 187 has a diameter that is greater than the diameter of the first diameter region 185 and a diameter that is smaller than the diameter of the third diameter region 188. In one or more embodiments, the second indicating element 180 includes a first diameter region 185 disposed adjacent to the distal end 189, second diameter region 187 disposed proximally adjacent to the first diameter region 185 and a third diameter region 188 disposed proximally adjacent to the second diameter region 187 and extending toward the proximal end 181. In a more specific embodiment, the diameter of the second diameter region 187 increases as it extends from the first diameter region 185 to the third diameter region 188. In an even more specific embodiment, the third diameter region 188 has a diameter that increases along its length in the distal or proximal direction.

In one or more embodiments, the third diameter region 188 has a diameter measured at the inside surface 184 that is sized to prevent the tip 150 of the fluid storage container 140 from entering or being inserted into the hollow interior 186 of the second indicating element. In embodiments of the second indicating element 180 that are composed of a plastic or polymeric material, the third diameter region 188 is sufficiently rigid to provide support to the second indicating element 180 to prevent deformation during use or, more specifically, upon application of a force on the hub and/or fluid storage container that causes the second indicating element 180 to advance distally over the first indicating element 170 and/or the protrusion 175. The third diameter region 188 of a specific embodiment may also have a diameter equal to or larger than the diameter of the first indicating element 170 and/or the diameter formed by the protrusion 175 and the first indicating element 170. In one or more embodiments, the diameter of the third diameter region 188 is greater than the diameter formed by the protrusion 175 such that the third diameter region 188 is permitted to advance distally past the protrusion 175. In such embodiments, advancement of the third diameter region 188 distally past the protrusion 175 indicates fluid tight engagement of the medical device and the fluid storage container and that no residual or additional force should be applied to the hub 160 in the proximal direction toward the fluid storage container or to the fluid storage container 140 in the distal direction toward the hub 160.

The first diameter region 185 forms an entrance angle 178 at the distal end 189 of the second indicating element 180 that permits the second indicating element 180 to move distally over the first indicating element 170, while forming line contact with the first indicating element 170 and the protrusion 175. It will be understood that prior to activation, line contact may be formed between the entrance angle 178 and the first indicating element 170. In a specific embodiment, the entrance angle 178 also forms line contact with the protrusion 175. In a more specific embodiment, line contact may be formed between the entrance angle 178 and the first diameter region 185 and the first indicating element 170 and the protrusion 175.

Figure 12:
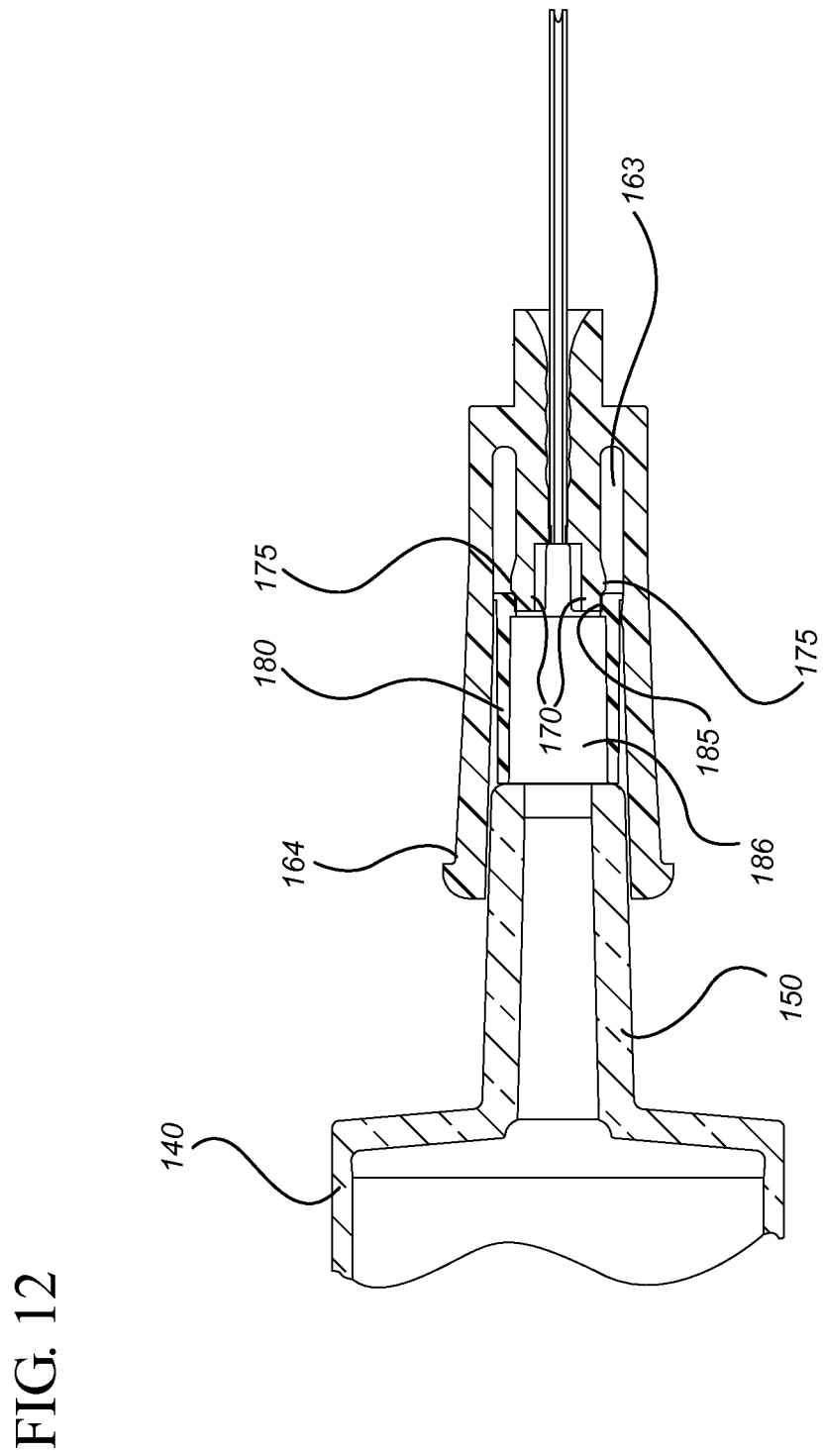
FIG. 12 illustrates FIG. 10 after application of an initial proximally directed force on the hub relative to the fluid storage container.
Figure 13:
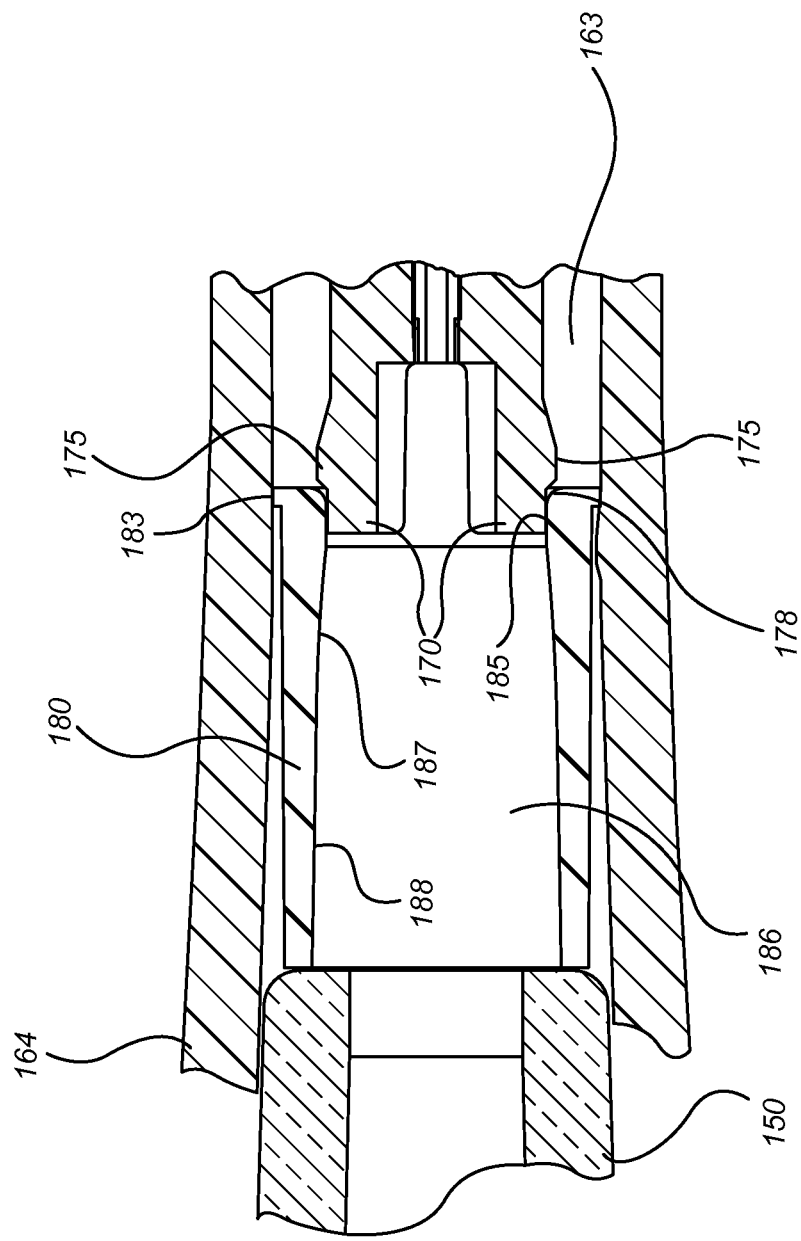
FIG. 13 is an enlarged view of FIG. 12.
Figure 14:
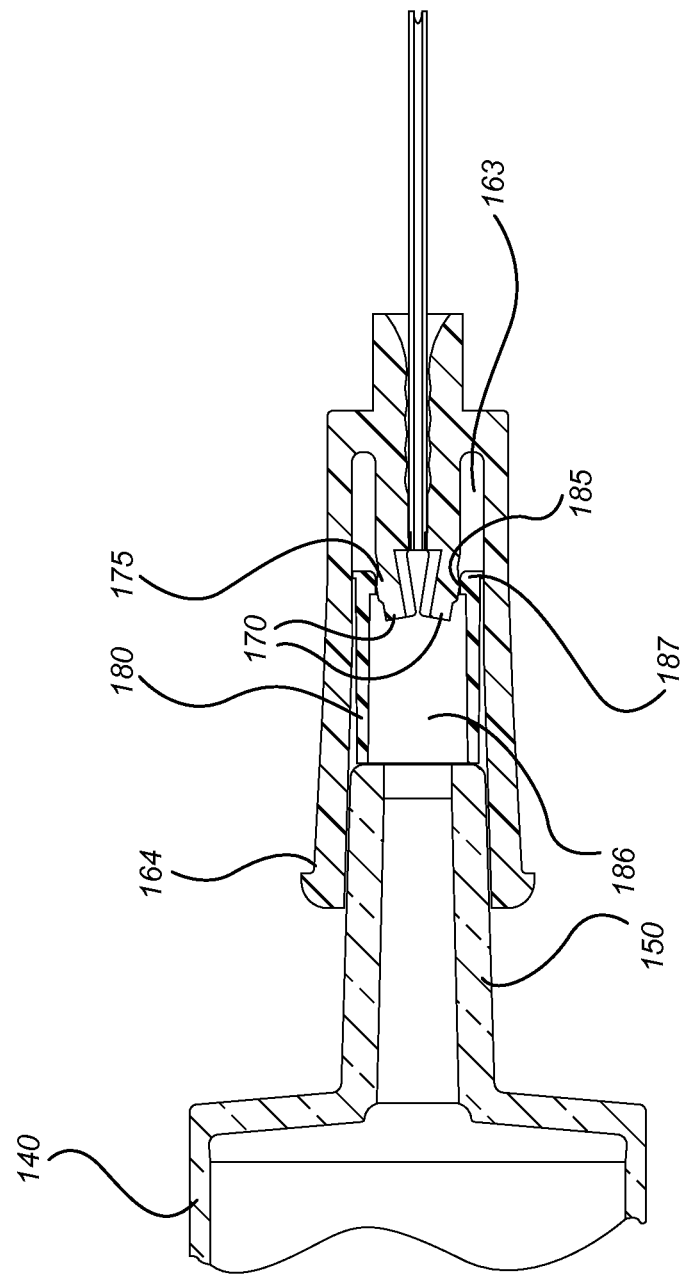
FIG. 14 illustrates FIG. 12 after continued application of a proximally directed force on the hub relative to the fluid storage container.
Figure 15:
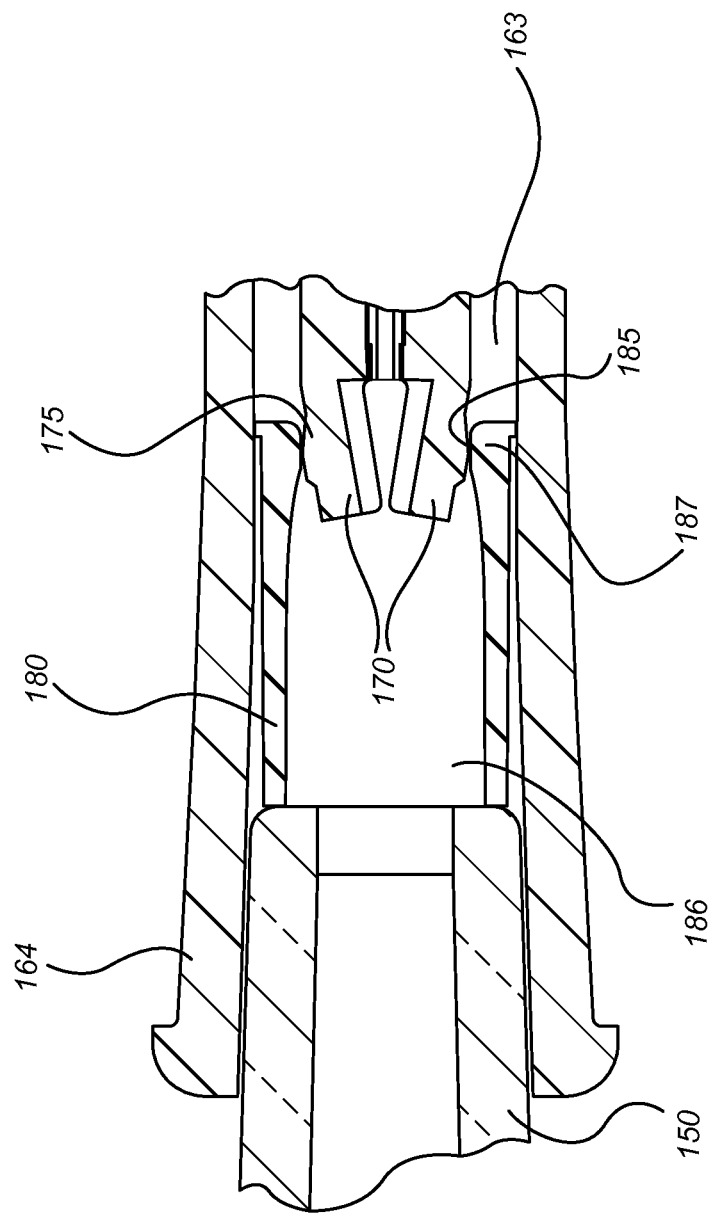
FIG. 15 is an enlarged view of FIG. 14.
Figure 16:
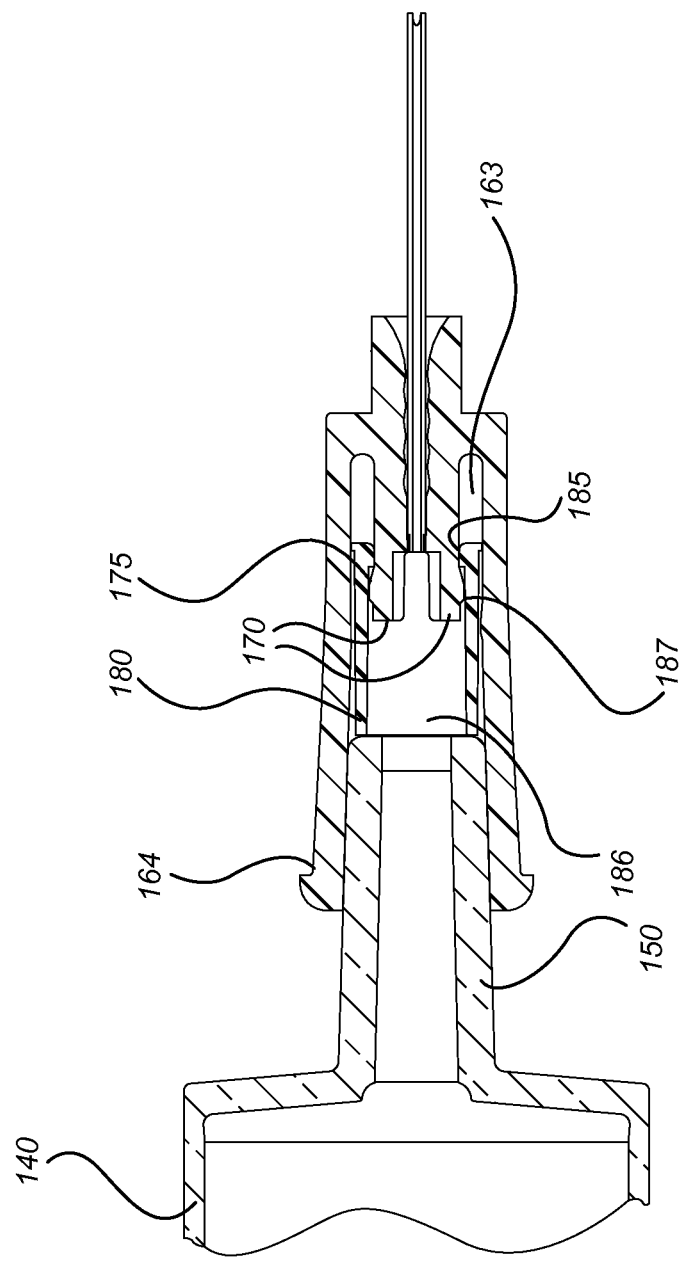
FIG. 16 illustrates FIG. 13 after the hub and the fluid storage container are in fluid-tight engagement.
Figure 17:
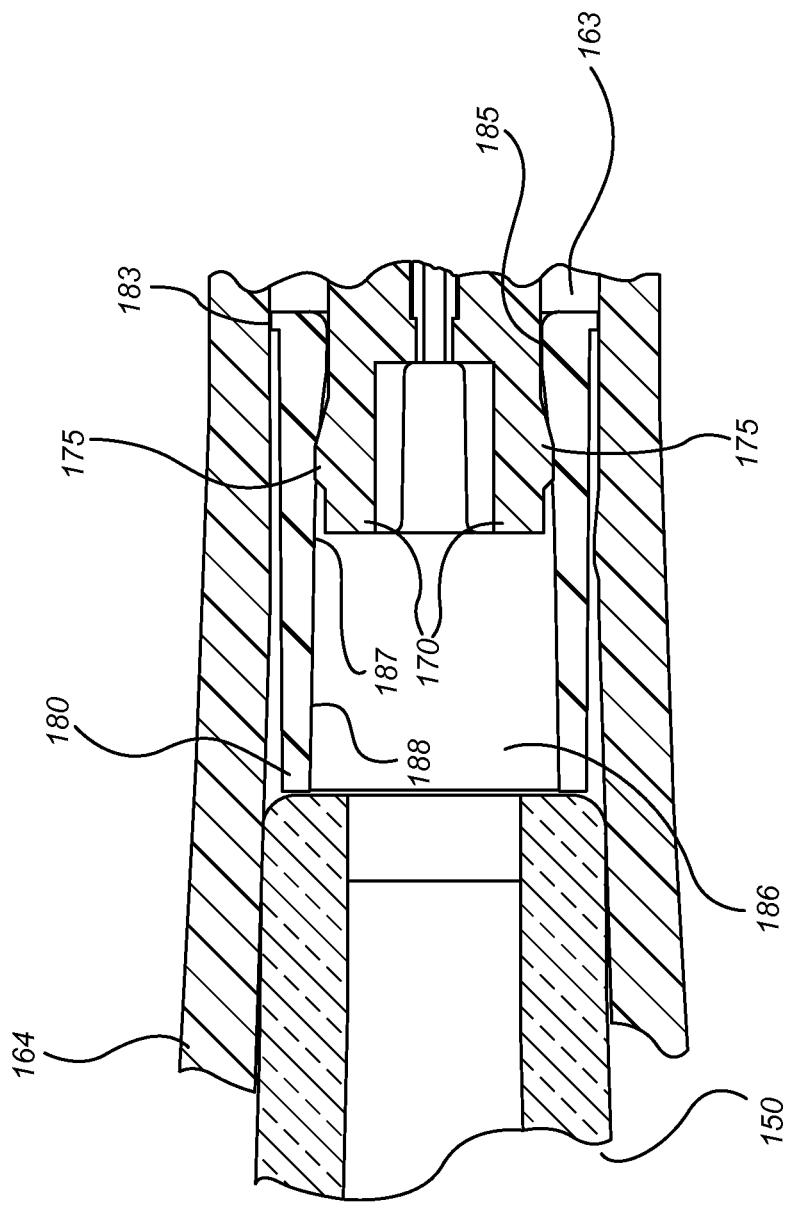
FIG. 17 is an enlarged view of FIG. 16.

As shown in the movements of the first and second indicating elements 170, 180 in FIGS. 10-17, the second indicating element 180 forms one or more line contact interactions with the first indicating element 180 and/or protrusion 175 as the second indicating element 180 enters the recess 163 and slides distally over the first indicating element 170. As shown in FIGS. 12-13, one or more line contact interactions are formed from the point at which the first indicating element 170 contacts the entrance angle 178 of the second indicating element 180. In one or more embodiments, the firsts indicating element 170 bends radially inwardly and permits the second indicating element 180 to further advance distally into the recess 163 while line contact is maintained between the first indicating element 170 and the second indicating element 180. As a proximally directed force is applied to the hub 160 toward the fluid storage container 140 or a distally directed force is applied to the fluid storage container 140 toward the hub 160, the second indicating element 180 continues to advance distally past the first indicating element 170 and forms one or more line contact interactions when the first indicating element 170 and/or protrusion 175 contacts the first diameter region 185 of the second indicating element 180, as shown in FIGS. 14-15. As the user continues to apply a proximally directed force to the hub 160 toward the fluid storage container 140 or a distally directed force is applied to the fluid storage container 140 toward the hub 160, one or more line contact interactions are formed as the first indicating element 170 and/or protrusion 175 contacts the second diameter region 187 and/or the third diameter region 188 of the second indicating element 180, as shown in FIGS. 16-17. In one or more embodiments, as the second diameter region 187 advances distally past the protrusion 175 and the third diameter region 188 begins to advance distally past the protrusion 175, line contact is no longer maintained. According to one or more embodiments, once the second indicating element 180 has moved distally past the protrusion 175 of the first indicating element, the protrusion 175 retains the second indicating element 180 within the recess 163 by preventing 180 and, specifically the first diameter portion 185, from moving in the proximal direction.

In a specific embodiment, the entrance angle 178 formed between first diameter region 185 at the distal end 189 of the second indicating element 180 has a radius that is larger than the height of the protrusion 185. In such embodiments, the larger radius of the second indicating element ensures the second indicating element 180 advances smoothly distally past the protrusion 175

According to one or more embodiments, the solid perimeter 190 formed by inside surface 184 of the second indicating element at the distal end 189 and the proximal end 181 maintains its shape or resists deformation as the second indicating element 180 moves distally over the first indicating element 170 and protrusion 175. The solid perimeter 190 of the second indicating element 180 forms a contact area between the inside surface 184 and the outside surface of the first indicating element 170 and/or the protrusion 175. For example, in embodiments which utilize a cylindrical second indicating element 180, the solid perimeter 190 maintains a circular shape as the second indicating element 180 moves distally over the first indicating element 170 and protrusion 175 and forms a circular contact area between the inside surface 184 and the outside surface of the first indicating element 170. In one or more embodiment, the rigidity of the solid perimeter 190 ensures that the second indicating element 180 maintains its shape and thus allows use of the medical device assembly with fluid-storage containers that require higher or increased engagement force to form a fluid-tight engagement between the medical device assembly and the fluid storage container 140. Interruptions in the solid perimeter 190 formed by the inside surface 184 at the distal end 189 and/or proximal end 181 of the second indicating element 180 cause the second indicating element 180 to deform as it moves distally over the first indicating element 170 and protrusion 175, causing variability in engagement forces required to connect the hub 160 and fluid storage container 140 in fluid-tight engagement. For example, the presence of interruptions in the solid perimeter 190 formed by the inside surface 184 of a second indicating element 180 having a cylindrical shape may cause the body 182 to deform such that the cross-section of the body 182 changes from a circular shape to an ellipsoidal shape. In another example, where the second indicating element 180 has a regular polygonal shape, interruptions in the solid perimeter 190 formed by the inside surface 184 may deform the body such that the cross-section of the body 182 changes from a regular polygonal to an irregular polygonal.

Figure 8:
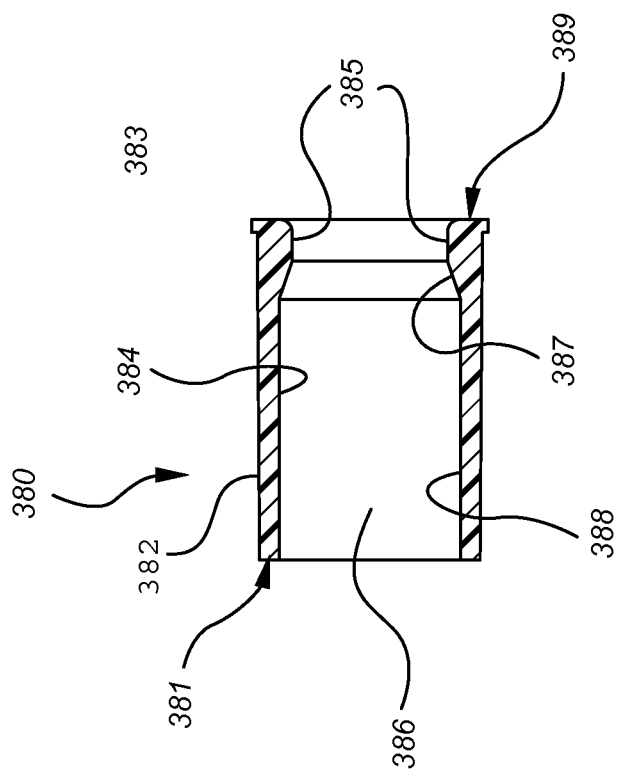
FIG. 8 is a cross-sectional view of an alternative embodiment of the second indicating element.

Interaction between non-conformal surfaces creates either a line or surface contact. The tapered geometry of the embodiments of the second indicating element 180 allows the formation of line contact interactions between the second indicating element 180 and the first indicating element 170. Line contact interactions distribute the stress and pressure applied to both surfaces among more than one point or location. This reduces the stress applied to any single point thereby reducing likelihood that a defect in one or both of the surfaces will result in a failure of the structural integrity of either part. Medical device assemblies which do not have a tapered second indicating element are likely to form only point or surface contacts with the first indicating element. In these assemblies the stress or force applied to both surfaces is not distributed According to one or more embodiments of the present invention, the inside surface 184 of the second indicating element 180 is further contoured to maintain line-contact with the first indicating element 170 as the second indicating element 180 moves distally over the first indicating element 170 and the protrusion 175. In one or more embodiments, once the second diameter region 187 advances distally past the protrusion 175, there is no contact between the protrusion 175 and second indicating element 180. Specifically, the entrance angle 178, first diameter region 185, second diameter region 187 and the third diameter region 188 are shaped to create line contact between the second indicating element 180 and the first indicating element 170 and the protrusion 175 throughout the range of distal movement of the first diameter region 185 and second diameter region 187 distally past the protrusion 175 of the first indicating element An alternative embodiment of the second indicating element 380 is shown in FIG. 8. The second indicating element 380 has a body 382 extending from an open distal end 389 to an open proximal end 381. The body 382 includes an inside surface 384 defining a hollow interior 386 and a lip 383 outwardly radially extending from the outside surface of the body 382. The inside surface 384 includes a tapered portion 385 adjacent the open distal end 389, a ramped portion 387 proximally adjacent to the tapered diameter portion 385, an enlarged portion 388 adjacent the open proximal end 381. The ramped portion 387 has an axial length extending from the tapered portion 385 toward the enlarged portion 388 such that the cross-sectional width measured at the inside surface 384 increases along the ramped portion 387 from the tapered portion 385 toward the enlarged portion 388. In this embodiment, the length of the ramped portion 387 is reduced in length such that the change in cross-sectional width measured at the inside surface 384 at the tapered portion 385 and the enlarged portion 388 is more abrupt or less gradual. In such embodiments, fluid-tight engagement of the hub and the fluid storage device provides more noticeable tactile feedback, while maintaining one or more line contact interactions between the first indicating element and the second indicating element 380. For example, upon advancement of the tapered portion 385 distally past the first indicating element and the protrusion creates a snappier or crisper engagement. This enhanced tactile feedback is believed to be produced from the expansion of the cross-sectional width measured from the inside surface 384 upon advancement of the tapered portion 385 distally past the protrusion with more rapid alignment of the protrusion with the enlarged portion 388.

The second indicating element of one or more embodiments described herein may be formed from a plastic material or from metal. In one or more embodiments, the second indicating element is injection molded using an injection moldable plastic such as polypropylene, polyethylene, polycarbonate or combinations thereof. As discussed above, the inside surface of the second indicating element forms one or more line contact interactions as the second indicating element advances distally over the first indicating element. It is believed that line contact interactions reduce sensitivity to molding defects on the protrusion and/or the first indicating element. The line contact interactions are also believed to reduce deformation of the inside surface of embodiments of second indicating element as it passes distally over the protrusion.

Previous attempts at providing a means for indicating fluid-tight engagement often utilize elements with abrupt changes in diameter, structural angles and contact interactions, to provide sufficient tactile feedback to the user. Such attempts discouraged the use of more gradual changes in diameter or other structural features. These attempts also utilize rigid materials to enhance tactile feedback and incorporate structural gaps in the body of the elements to accommodate for potential skiving and unpredictable engagement forces that may result from the rigidity and/or stiffness of the materials utilized. Further, the need to produce tactile feedback also limits the range of materials that can be used to produce the desired structures Previous attempts at improving connection mechanisms for securely connecting a hub to fluid storage containers in fluid-tight engagement and mechanisms to indicate such engagement between a hub and fluid container have focused on modifying the type of materials utilized for the first and/or second indicating elements. Modifying materials was also thought to result in additional benefits such as reducing the weight of the medical device assembly and allowing the use of other methods of production, such as molding, that can increase production capacity more easily than other methods of production, such as stamping used to form metallic components. The variation in production methods also permits a greater selection of materials. Specific attempts at modifying the materials used to form the first and/or second indicating elements focused on using a more rigid plastic material to manufacture the first and/or second indicating elements. Such materials were believed to provide a better indicator of the engagement force needed to form fluid-tight engagement between the hub and the fluid storage container. In such attempts, however, the more rigid plastic did not have a direct consequence on the engagement forces needed for the fluid-tight engagement of the hub to the fluid storage container. Further use of varying materials caused additional problems such as variability in engagement forces of the first indicating element and second indicating element, which prevented accurate indication of fluid-tight engagement between the hub and the fluid storage container.

Modifying the shape of the components, for example, by utilizing the tapered design for the second indicating element described herein, mitigated these problems. The solid perimeter 190 design of the second indicating element further improved manufacturability and allowed the selection and use of more elastic materials, which reduces the dependency on exact dimensions. Further, the surface finishes of the outside surface of the first indicating element and the inside surface of the second indicating element can be modified to ensure more consistent interaction between the first and second indicating elements.

In one or more embodiments, second indicating elements 180 manufactured by injection molding are substantially free of structural projections caused by other manufacturing methods that have limited application based on the material used. Such structural projections include projections that extend radially outwardly from the body at the distal end and/or proximal end, that may cause skiving of the hub or other increases in the engagement force required to form a fluid-tight engagement between the hub and tip.

In one or more embodiments, the sidewall 164 of the hub, the first indicating element 170 and/or the second indicating element 180 may also be shaped and configured to reduce dead space or unoccupied space between the tip 150 and the passageway 130. In previous attempts at a connection mechanism to indicate fluid-tight engagement between the hub and the fluid-storage container, gaps were included in the perimeter at the openings of the second indicating element as a result of limited production means and materials. In such embodiments the open gaps resulted in increased dead space within the hub when attached to a fluid storage device. Embodiments of the second indicating element 180 which include a solid and continuous body 182 reduce dead space within the cavity when the hub is attached to the fluid-storage device. In one or more embodiments, the length of the first indicating element 170 may be adjusted to permit the distal end of one or more embodiments of the second indicating element described herein to advance into the recess 163 formed between the first indicating element 170 and the sidewall 164 until it contacts the distal end 169 of the hub 160. In such embodiments, the length of the first indicating element 170 and the movement of the distal end of the second indicating element provide additional indication of fluid tight engagement between the hub 160 and the tip or fluid storage container by preventing the user from applying a force on the hub in the proximal direction or the fluid storage container in the distal direction. In an alternative embodiment, the length of the first indicating element 170 may be adjusted to allow the use of second indicating elements having different lengths. In one or more embodiments, the length of the first indicating element 170 is sufficiently long to permit the second indicating element to advance distally past the protrusion 175 without interference or being blocked by the distal end 169 of the hub 160. Alternatively, the length of the body 182 of the second indicating element 180 may be reduced to reduce dead space between the tip 150 and the passageway 130 The sidewall 164 may also be adjusted or modified to reduce or increase the length and/or dimensions of the recess 163, however, the length of the recess 163 should permit the second indicating element 180 to advance distally past the protrusion 175.

Figure 18A:
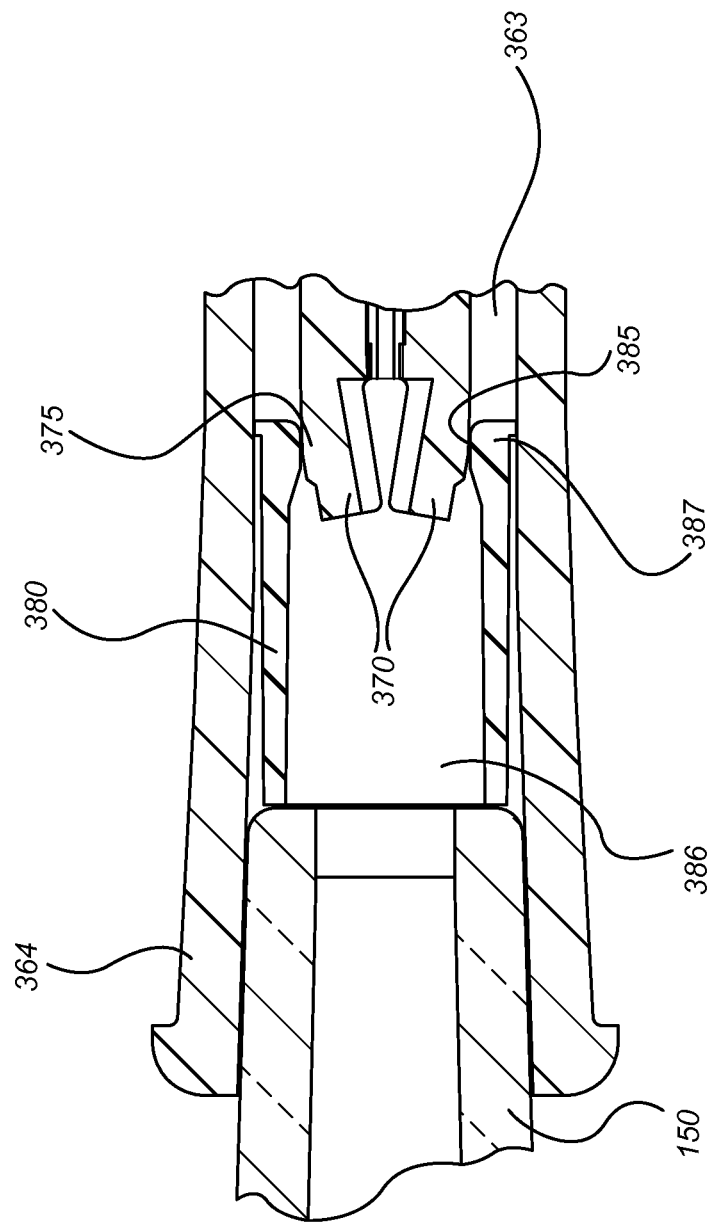
FIG. 18A is an cross-sectional view of the second indicating element of FIG. 8 advancing distally past an alternative embodiment of the hub upon application of a proximally directed force on the hub relative to the fluid storage container.
Figure 18B:
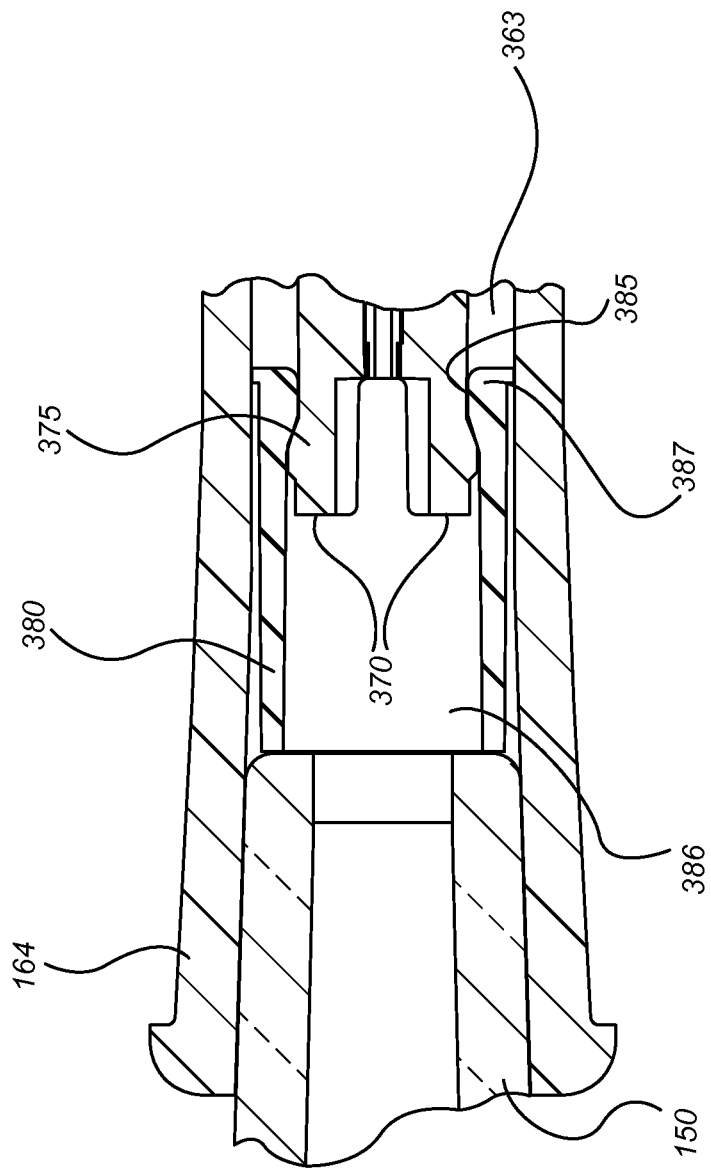
FIG. 18B is a cross-sectional view of the second indicating element of FIG. 8 advancing distally past the alternative embodiment of the hub of FIG. 18A upon continued application of a proximally directed force on the hub relative to the fluid storage container.
Figure 19:
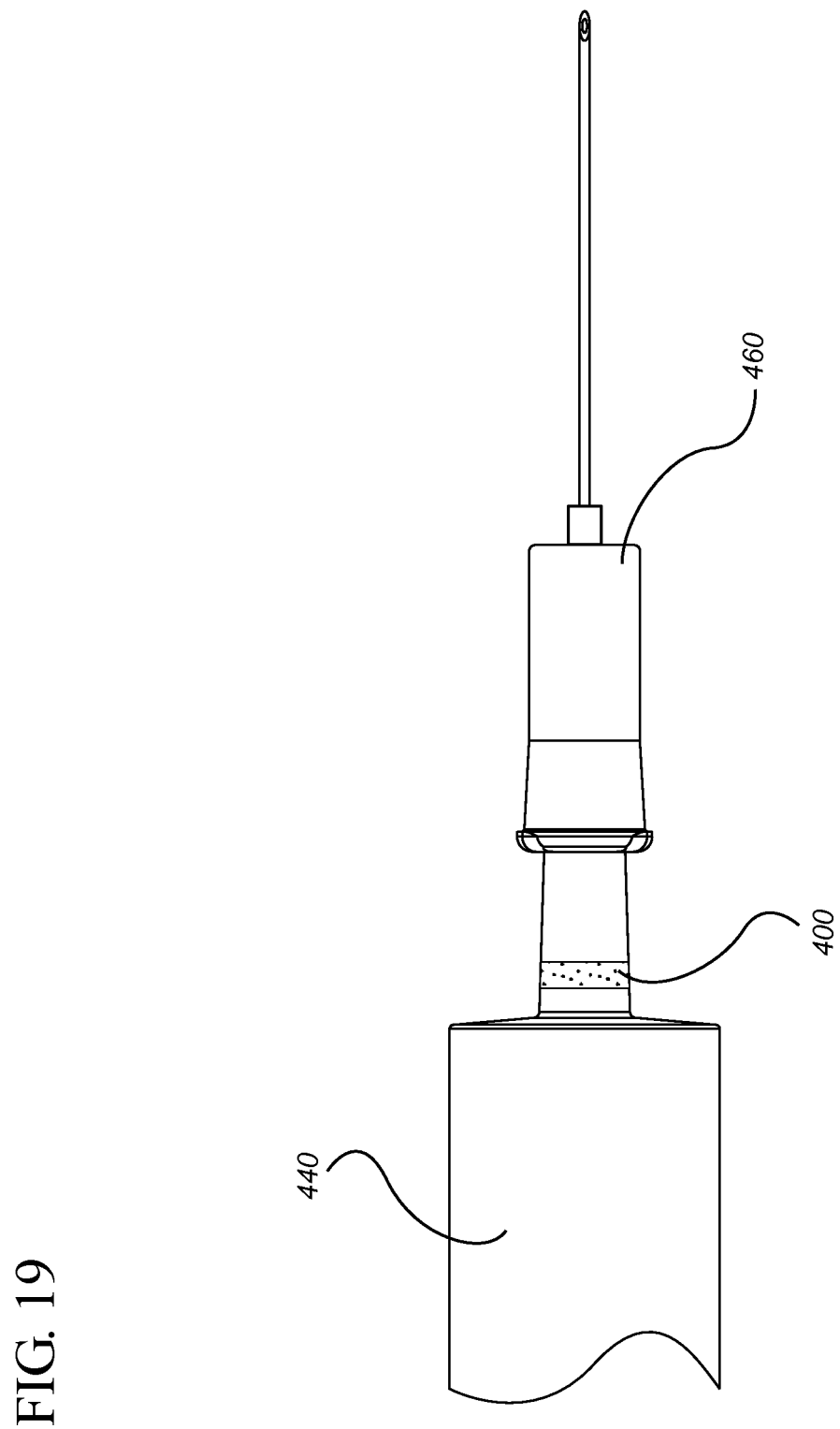
FIG. 19 illustrates a partially assembled view of a medical device according to a second embodiment of the invention.
Figure 20:
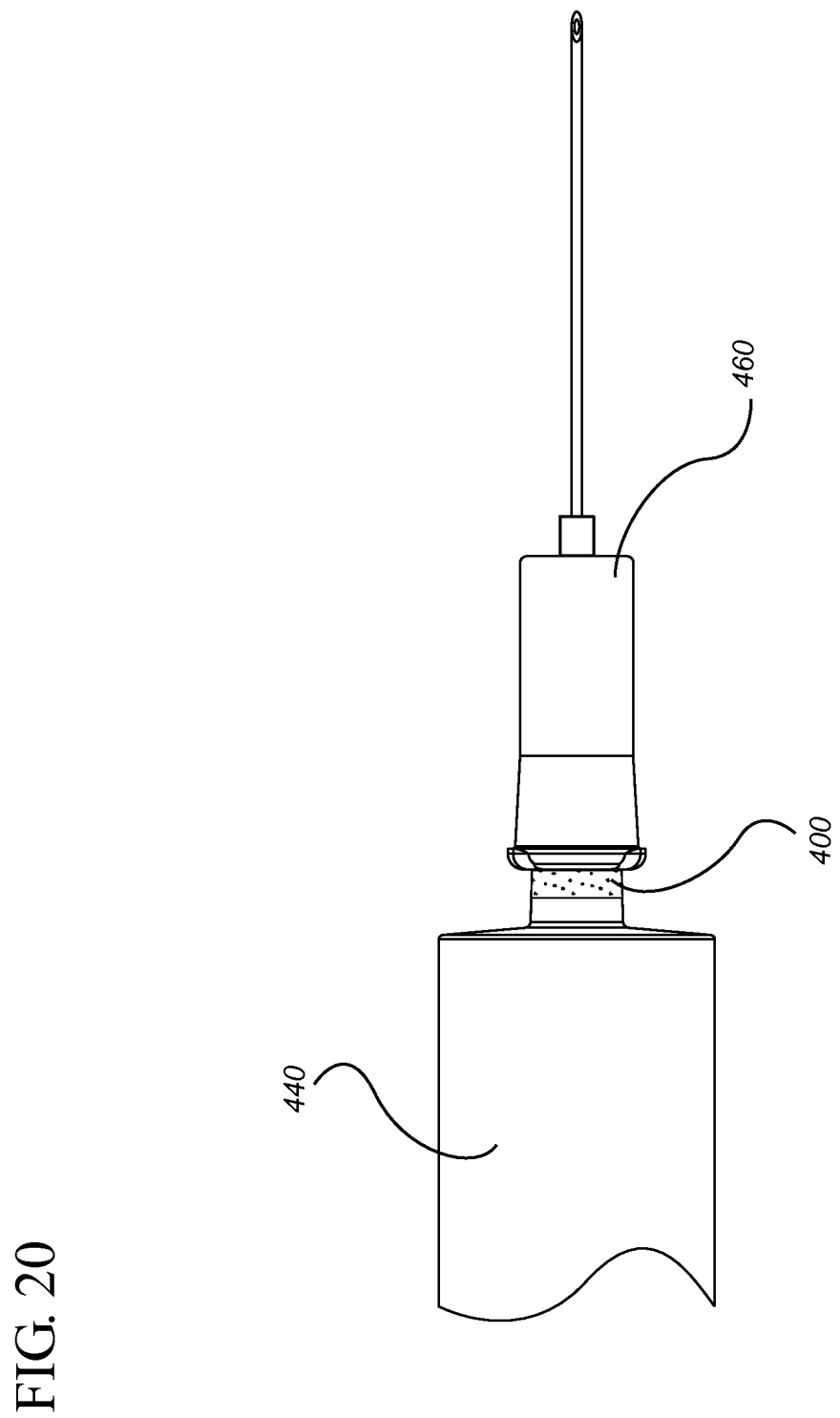
FIG. 20 shows the medical device of FIG. 19 in an optimal assembly.

An alternative embodiment of the hub 360 is shown in FIGS. 18A and 18B. The hub 360 includes a sidewall 364 and a first indicating element 370 that is flexible and which forms a recess 363 with the sidewall 364. As the user applies the pre-determined force on the hub 360 to form a fluid-tight engagement between the hub 360 and a fluid storage container, the first indicating element 380 flexes inwardly toward the passageway 330 to permit the body 382 of the second indicating element to advance distally over the first indicating element 370 and/or protrusion 375 into the recess 363. The ability of the first indicating element 370 to resume its original shape creates a tactile feedback for the user of fluid-tight engagement between the hub 360 and the fluid storage container. As shown in FIGS. 18B and A, the ramped portion 387 of the second indicating element 280 has a reduced length that results in a more dramatic increase in diameter or cross-sectional width measured at various points along the inside surface of the second indicating element. In such embodiments, the first indicating element is permitted to flex and relax more rapidly thereby producing enhanced tactile feedback for the user of fluid-tight engagement between the hub and the fluid storage container.

According to an alternative embodiment, the body of the second indicating element may be flexible and may flex as the second indicating element advances distally over the first indicating element and/or protrusion. In such embodiments, the solid perimeter may be rigid and retains its shape as the second indicating element advances distally over the first indicating element. In a more specific embodiment, one of the first indicating element and the second indicating element has greater flexibility that the other of the first indicating element and the second indicating element. In an even more specific embodiment, one of the first indicating element and second indicating element is flexible while the other of the two is relatively inflexible in comparison to the flexible element.

In embodiments where there is gradual increase in diameter or cross-sectional width measured at various points along the length of the inside surface of the second indicating element, the first indicating element and/or the second indicating element can provide tactile feedback through the use of different materials with different flexibility or rigidity that permit the flexed element to resume its original shape after the second indicating element advances distally past the protrusion of the first indicating element.

A second aspect of the present invention pertains to an indication system for use with the medical device assemblies described herein during attachment to a fluid storage container, for example, the fluid storage container 140 shown in FIG. 1. The indication system provides visual indication of optimal engagement or optimal degree of press-fit or interference fit has been achieved during connection of the hub, for example, the hub 160 shown in FIG. 1, and the fluid storage container. Specifically, the indication system provides visual indication of over-tightening, under-tightening and optimal tightening of the luer slip connection between hub 160 and the fluid storage container 140. Over-tightening of the hub 160 and fluid storage container luer slip may cause excessive compressive force at the joint or mating interface between the hub 160 and fluid storage container 140. This excessive compressive force can later require the user to apply a large amount of force to disassemble the hub 160 from the fluid storage container 140. Under-tightening of the hub 160 and fluid storage container luer slip connection may compromise the effectiveness of the fluid-tight engagement or seal formed by the connection and may result in leakage of the medication being delivered from within fluid storage container through the hub 160 or even complete separation of the hub 160 from the fluid storage container 140.

Figure 21:
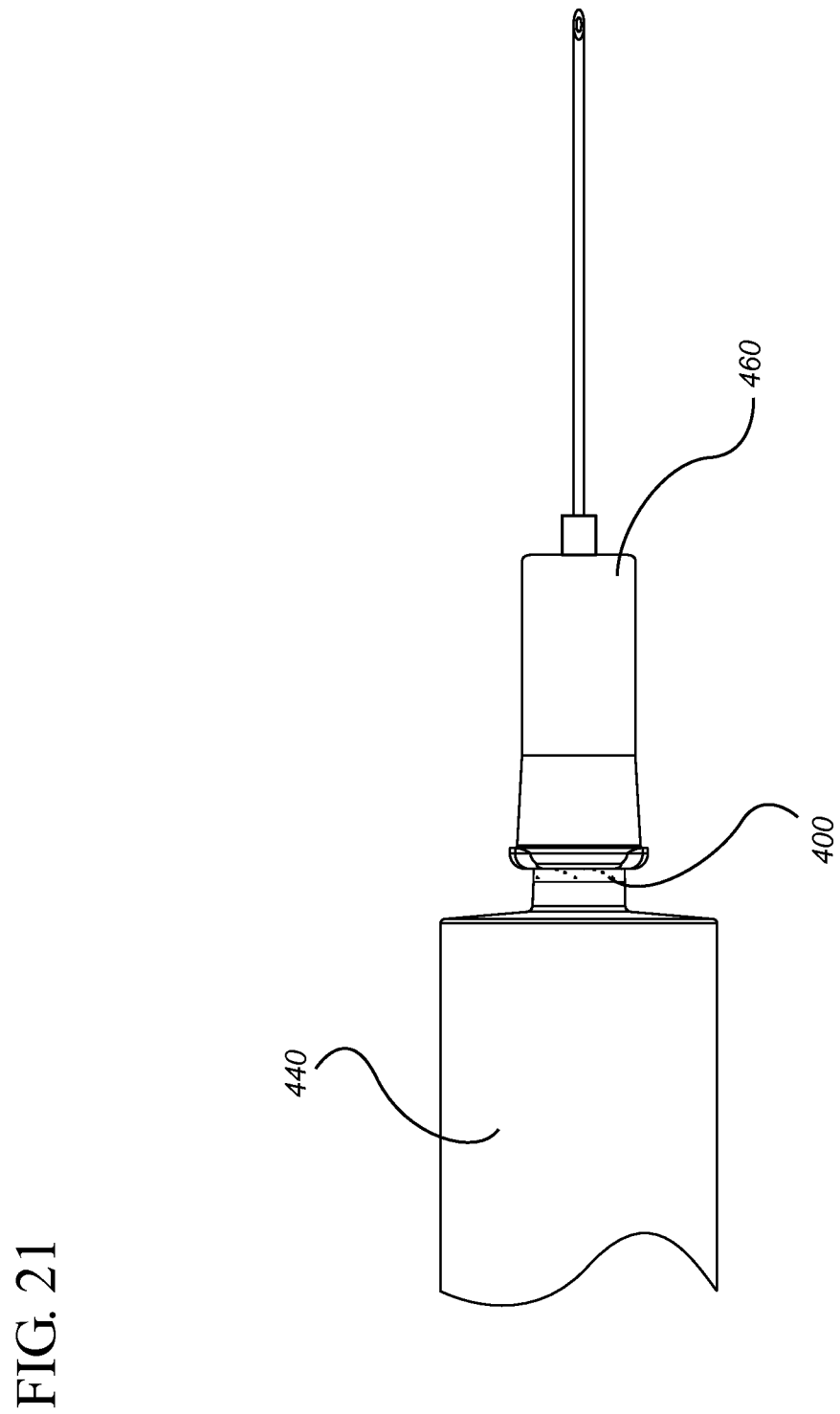
FIG. 21 shows the medical device of FIG. 19 in an over-tightened assembly.
Figure 22:
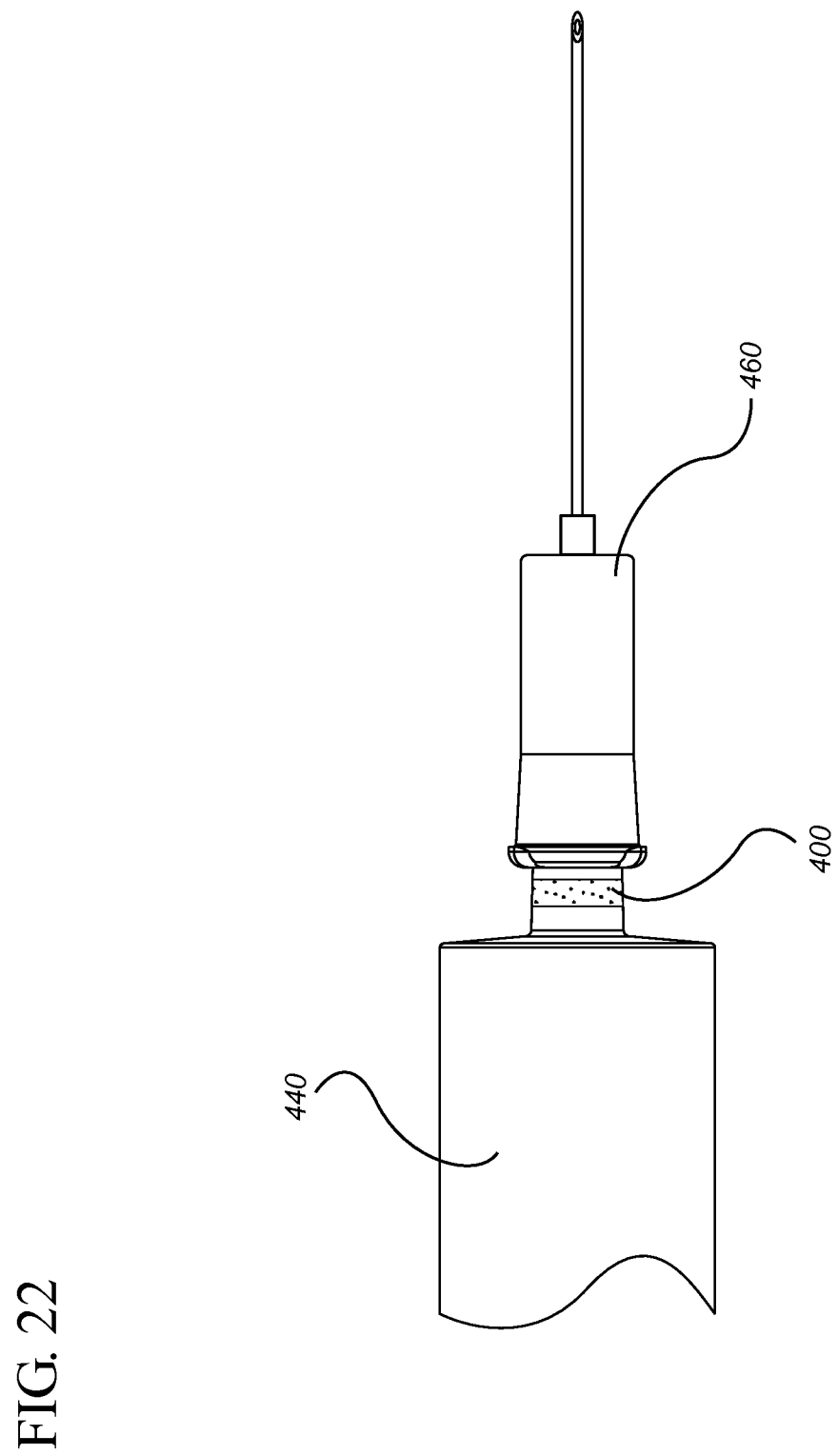
FIG. 22 shows the medical device of FIG. 19 in an under-tightened assembly.

The indication system of the embodiment shown in FIGS. 19-22 includes a visual indicator 400 that is added to the fluid storage container 440, for example, along the circumference of the tip or opening of the fluid storage container 440. In one or more embodiments, the visual indicator is a colored region that is printed or over-molded onto the fluid storage container. Other means known in the art may be utilized to apply or form the visual indicator on the fluid storage container 440. During attachment of the hub 460 to the fluid storage container 440, a force is applied to the hub 460 in the proximal direction relative to the fluid storage container 440. After application of the force, the position of the hub 460 relative to the visual indicator 400 indicates whether adequate force has been applied to the hub to obtain optimal tightening. As shown more clearly in FIG. 20, optimal engagement is indicated by alignment of the visual indicator 400 directly adjacent to the hub 460. FIG. 21 illustrates overlap of the visual indicator 400 and hub 460 indicating an over-tightened connection between the hub 460 and the fluid storage container 440. FIG. 22 illustrates a space between the visual indicator 400 and the hub 460, indicating an under-tightened connection between the hub 460 and the fluid storage container 440.

In a specific embodiment, the visual indicator 400 includes three separate stripes (not shown) formed at three different locations from near the opening of the fluid storage container and proximally along the length of the fluid-storage. In a more specific embodiment, the three stripes may have different colors. In such embodiments, the first stripe disposed closest to the opening of the fluid storage container is the first stripe and may be red in color, the second stripe disposed proximally adjacent to the first stripe may be green in color and the third stripe disposed proximally adjacent to the second stripe may be yellow in color. As a force is applied to the hub in the proximal direction toward the fluid storage container or a force is applied to the fluid storage container in the distal direction toward the hub, visibility of the first, second and third stripes (or the red, green and yellow stripes) indicates under tightening and that additional force must be applied to the hub and/or fluid storage container. Visibility of the second and third stripes (or the green and yellow stripes) indicates optimal tightening while visibility of only the third stripe (or the yellow stripe) indicates over tightening. In one or more embodiments, the indication system of FIGS. 19-22 may be useful in providing visual indication of fluid-tight engagement between the medical assemblies described herein that provide reduced tactile feedback of fluid-tight engagement. Examples of such embodiments assemblies with a second indicating element 180 that does not include a third diameter region 188 or that includes a second diameter region 187 having a length sufficiently long enough that the change in diameter from the first diameter region and the remaining length of the second indicating element is gradual or less abrupt. Alternatively, the indication system of FIGS. 19-22 may also be utilized with embodiments with enhanced tactile feedback to provide an additional indication of fluid-tight engagement between the medical device assembly and the fluid storage container.

A third aspect of the present invention pertains to methods of using the medical devices described herein. In one or more embodiments, the method includes providing a hub including a sidewall having an inside surface defining a cavity, an open proximal end, a distal end having an opening therethrough in fluid communication with the cavity and a second indicating element disposed within the cavity. The method further includes positioning the hub such that the open proximal end is aligned with the opening of a fluid storage container and applying a proximally directed force on the hub or applying a distally directed force on the fluid storage container such that the opening of the fluid storage container is disposed within the cavity and abuts the second indicating element. The method further includes applying a continuous force in the proximal direction on the hub and/or in the distal direction on the fluid storage container to force the second indicating element to advance distally further into the cavity and engage with the hub. In embodiments of the medical device which utilize a first indicating element extending from the distal end of the hub into the cavity, the method includes applying a continuous force on the hub in the proximal direction toward the fluid storage container and/or on the fluid storage container in the distal direction toward the hub such that the second indicating element envelopes the first indicating element and enters into the recess formed between the first indicating element and the hub, until the hub and fluid storage device are in fluid-tight engagement.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A medical device for use with a fluid storage container comprising:
   a hub including a sidewall having an inside surface defining a cavity, an open proximal end, and a distal end having an opening therethrough in fluid communication with the cavity;
   a first indicating element having a distal end attached to the distal end of the hub and a free proximal end extending into the cavity, the first indicating element forming a peripheral recess with the sidewall of the hub; and
   a second indicating element disposed in the cavity of the hub including an open proximal end, an open distal end and a body extending from the open proximal end of the second indicating element to the open distal end of the second indicating element, the body having an inside surface of the body defining a hollow interior for enveloping the first indicating element to permit the body to enter the recess upon application of a distally directed force on the second indicating element, the inside surface of the body defining a first diameter region, a second diameter region and a third diameter region, the second diameter region has a diameter that is greater than a diameter of the first diameter region and a diameter that is smaller than a diameter of the third diameter region, wherein the first diameter region forms an entrance angle at the distal end of the second indicating element to permit the second indicating element to move distally over the first indicating element, wherein the entrance angle, the first diameter region, the second diameter region and the third diameter region create line contact between the second indicating element and the first indicating element throughout a range of distal movement of the first diameter region and the second diameter region distally past the first indicating element.

2. The medical device of claim 1, wherein the first diameter region has a narrowed cross-sectional width or diameter compared to the second diameter region measured along a circumference of the inside surface of the body at one or more points along a axial length of the body.

3. The medical device of claim 1, wherein the first diameter region of the second indicating element is disposed adjacent to the distal end of the second indicating element, the second diameter region is disposed proximally adjacent to the first diameter region and the third diameter region is disposed proximally adjacent to the second diameter region and extending toward the proximal end of the second indicating element.

4. The medical device of claim 1, wherein the diameter of the second diameter region increases as it extends from the first diameter region to the third diameter region.

5. The medical device of claim 1, wherein the third diameter region has a diameter that increases along its length in a proximal direction.

6. The medical device of claim 1, wherein the third diameter region has a diameter measured at the inside surface of the body to prevent a tip of a fluid storage container from entering into the hollow interior of the second indicating element.

7. The medical device of claim 1, wherein the first indicating element comprises an outwardly radially extending protrusion that prevents the body of the second indicating element from entering the recess until a pre-determined distally-directed force is applied to the second indicating element.

8. The medical device of claim 7, wherein the third diameter region has a diameter equal to or larger than a diameter of the first indicating element.

9. The medical device of claim 7, wherein the third diameter region has a diameter equal to or larger than a diameter formed by the protrusion and the first indicating element.

10. The medical device of claim 7, wherein the entrance angle forms a line contact with the protrusion.

11. The medical device of claim 1, wherein the open distal end of the second indicating element comprises a continuous perimeter that maintains a circular form upon application of a distally directed force on the second indicating element until the hub and the fluid storage container are in fluid-tight engagement.

12. The medical device of claim 1, further comprising a needle cannula attached to the distal end of the hub and extending in a distal direction, the needle cannula having a proximal end, a distal end and a lumen therethrough in fluid communication with the cavity.

13. The medical device of claim 12 further comprising a safety cap covering the needle cannula and wherein the hub comprises a coaxial wall extending from the distal end of the hub forming a channel between the coaxial wall and the sidewall for receiving the safety cap.

14. The medical device of claim 1, wherein the fluid storage container includes a tip having a visual indicator that is fully visible prior to fluid-tight engagement of the fluid storage container and the cavity of the hub wherein the visual indicator has a predetermined portion which is visible upon fluid-tight engagement of the fluid storage container and the hub.

15. The device of claim 1, wherein fluid-tight engagement of the hub and the fluid storage container produces tactile feedback.

16. The medical device of claim 1, wherein the fluid storage container includes a male luer connector having a visual indicator that is fully visible prior to a fluid-tight engagement of the fluid storage container and the cavity of the hub and wherein the visual indicator has a predetermined portion which is visible after fluid-tight engagement of the fluid storage container and the hub.

* * * * *